United States Patent
Laurent et al.

(10) Patent No.: US 11,896,232 B2
(45) Date of Patent: Feb. 13, 2024

(54) TISSUE STABILIZING FEATURES FOR CIRCULAR SURGICAL STAPLER

(71) Applicant: Cilag GmbH International, Zug (CH)

(72) Inventors: Ryan J. Laurent, Loveland, OH (US); Bradley A. Arnold, Mason, OH (US); Taylor W. Aronhalt, Loveland, OH (US); Sean M. Starrett, Baltimore, OH (US); Logan R. Rose, Loveland, OH (US); Anthony Nguyen, West Chester, OH (US)

(73) Assignee: Cilag GmbH International, Zug (CH)

( * ) Notice: Subject to any disclaimer, the term of this patent is extended or adjusted under 35 U.S.C. 154(b) by 10 days.

(21) Appl. No.: 17/534,653

(22) Filed: Nov. 24, 2021

(65) Prior Publication Data

US 2023/0157693 A1    May 25, 2023

(51) Int. Cl.
*A61B 17/3205* (2006.01)
*A61B 17/115* (2006.01)

(52) U.S. Cl.
CPC ...... *A61B 17/1155* (2013.01); *A61B 17/3205* (2013.01)

(58) Field of Classification Search
CPC .......................... A61B 17/1155; A61B 17/3205
See application file for complete search history.

(56) References Cited

U.S. PATENT DOCUMENTS

| | | |
|---|---|---|
| 4,592,354 A | 6/1986 | Rothfuss |
| 5,292,053 A | 3/1994 | Bilotti et al. |
| 5,333,773 A | 8/1994 | Main et al. |
| 5,350,104 A | 9/1994 | Main et al. |
| 5,452,837 A * | 9/1995 | Williamson, IV ........... A61B 17/07207 227/176.1 |
| 5,533,661 A | 7/1996 | Main et al. |

(Continued)

FOREIGN PATENT DOCUMENTS

| | | |
|---|---|---|
| CA | 2553139 A1 | 2/1996 |
| EP | 3225192 A1 | 10/2017 |

(Continued)

OTHER PUBLICATIONS

International Search Report and Written Opinion dated Apr. 26, 2023 for Application No. PCT/IB2022/061217, 23 pgs.

*Primary Examiner* — Nathaniel C Chukwurah
(74) *Attorney, Agent, or Firm* — Frost Brown Todd LLP

(57) ABSTRACT

A surgical instrument includes a stapling assembly and an anvil configured to cooperate to compress, staple, and cut tissue. The stapling assembly includes a deck member having a deck surface that faces distally and includes a plurality of staple openings configured to receive a plurality of staples, and a knife member having a distal end that defines a cutting edge. The anvil includes an anvil surface having a plurality of staple forming pockets configured to form the staples, and a washer positioned adjacent to the anvil surface and having a proximal face. The cutting edge of the knife member is configured to cut through the tissue and the proximal face when the surgical instrument is fired. The proximal face includes a tissue gripping feature configured to stabilize and inhibit the tissue from translating across the washer and the anvil surface during firing.

20 Claims, 25 Drawing Sheets

(56) References Cited

U.S. PATENT DOCUMENTS

| | | | |
|---|---|---|---|
| 5,667,526 A * | 9/1997 | Levin | A61B 17/29 606/205 |
| 8,910,847 B2 | 12/2014 | Nalagatla et al. | |
| 9,539,021 B2 | 1/2017 | Mata et al. | |
| 9,713,469 B2 | 7/2017 | Leimbach et al. | |
| 9,743,946 B2 | 8/2017 | Faller et al. | |
| 9,907,552 B2 | 3/2018 | Measamer et al. | |
| 9,936,949 B2 | 4/2018 | Measamer et al. | |
| 10,045,780 B2 | 8/2018 | Adams et al. | |
| 10,709,452 B2 | 7/2020 | DiNardo et al. | |
| 11,179,177 B2 | 11/2021 | Olson | |
| 11,324,504 B2 | 5/2022 | Hontz et al. | |
| 2014/0175152 A1 | 6/2014 | Hess et al. | |
| 2015/0083772 A1 | 3/2015 | Miller et al. | |
| 2017/0281187 A1* | 10/2017 | Shelton, IV | A61B 17/3211 |
| 2018/0132848 A1* | 5/2018 | Miller | A61B 17/07207 |
| 2018/0132849 A1 | 5/2018 | Miller et al. | |

FOREIGN PATENT DOCUMENTS

| WO | WO 2016/189693 A1 | 12/2016 |
|---|---|---|
| WO | WO 2018/092273 A1 | 5/2018 |

\* cited by examiner

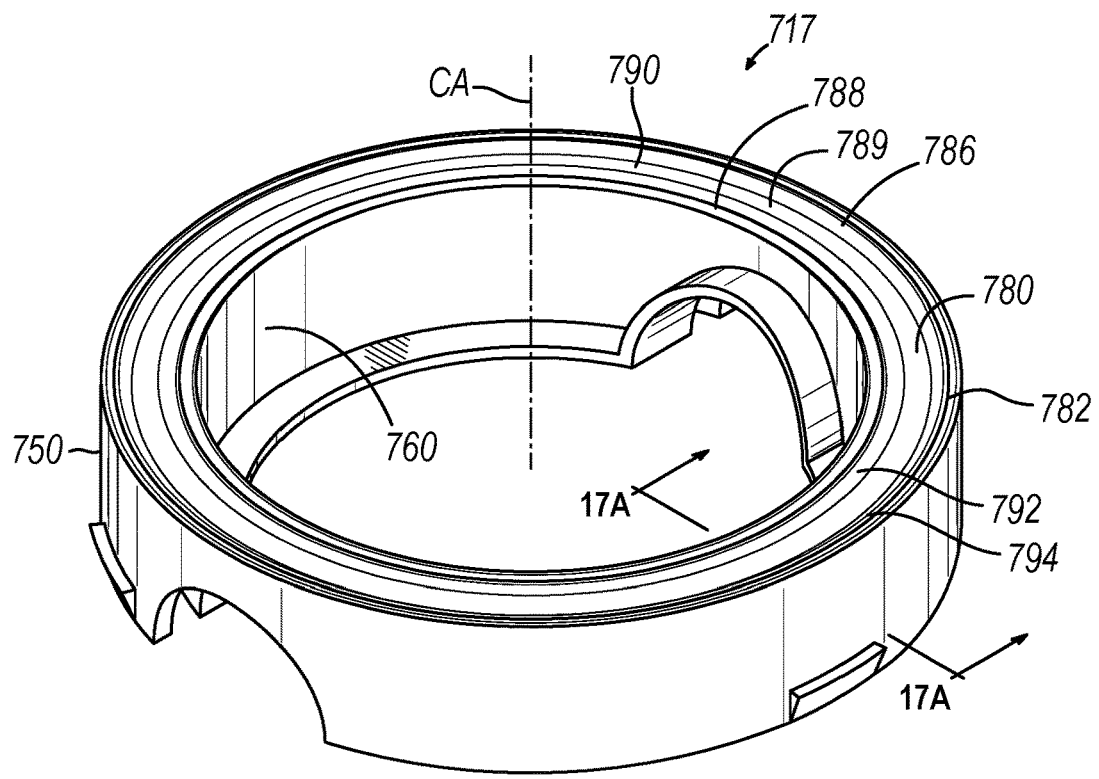
FIG. 16
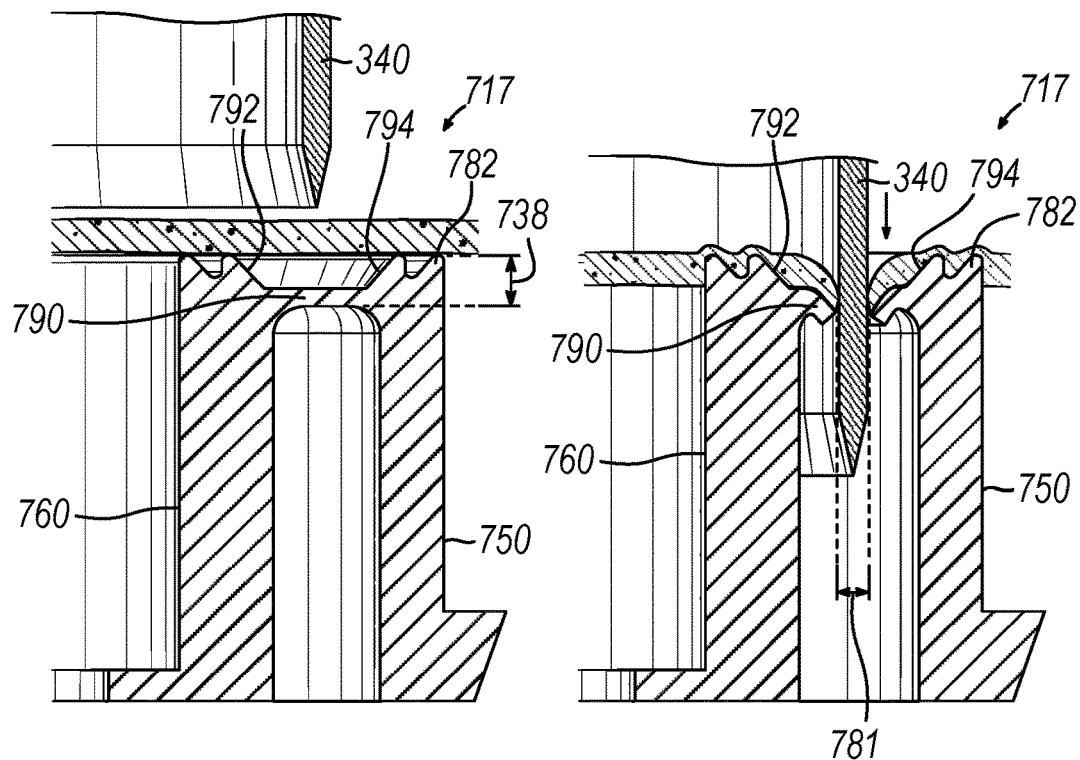
FIG. 17A      FIG. 17B

TISSUE STABILIZING FEATURES FOR CIRCULAR SURGICAL STAPLER

BACKGROUND

A circular surgical stapler may be used to form an anastomosis between two organ portions of a patient's digestive tract. Examples of circular surgical staplers are described in U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; U.S. Pub. No. 2018/0132849, entitled "Staple Forming Pocket Configurations for Circular Surgical Stapler Anvil," published May 17, 2018, now abandoned; and U.S. Pat. No. 10,709,452, entitled "Methods and Systems for Performing Circular Stapling," issued Jul. 14, 2020. The disclosure of each of the above-cited U.S. Patent Publications and U.S. Patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 16 depicts a perspective view of yet another exemplary washer for use with the anvil of FIG. 8, where the washer has a tissue gripping feature in the form of a plurality of annular ridges;

FIG. 17A depicts a partial cross-sectional side view of the washer of FIG. 16, taken along line 17A-17A of FIG. 16, with the knife member in a proximal pre-fired position and with other features of the corresponding end effector being omitted;

FIG. 17B depicts another partial cross-sectional side view of the washer of FIG. 16, taken along line 17A-17A of FIG. 16, with the knife member in a distal fired position after transecting the washer and tissue;

Figure 1:
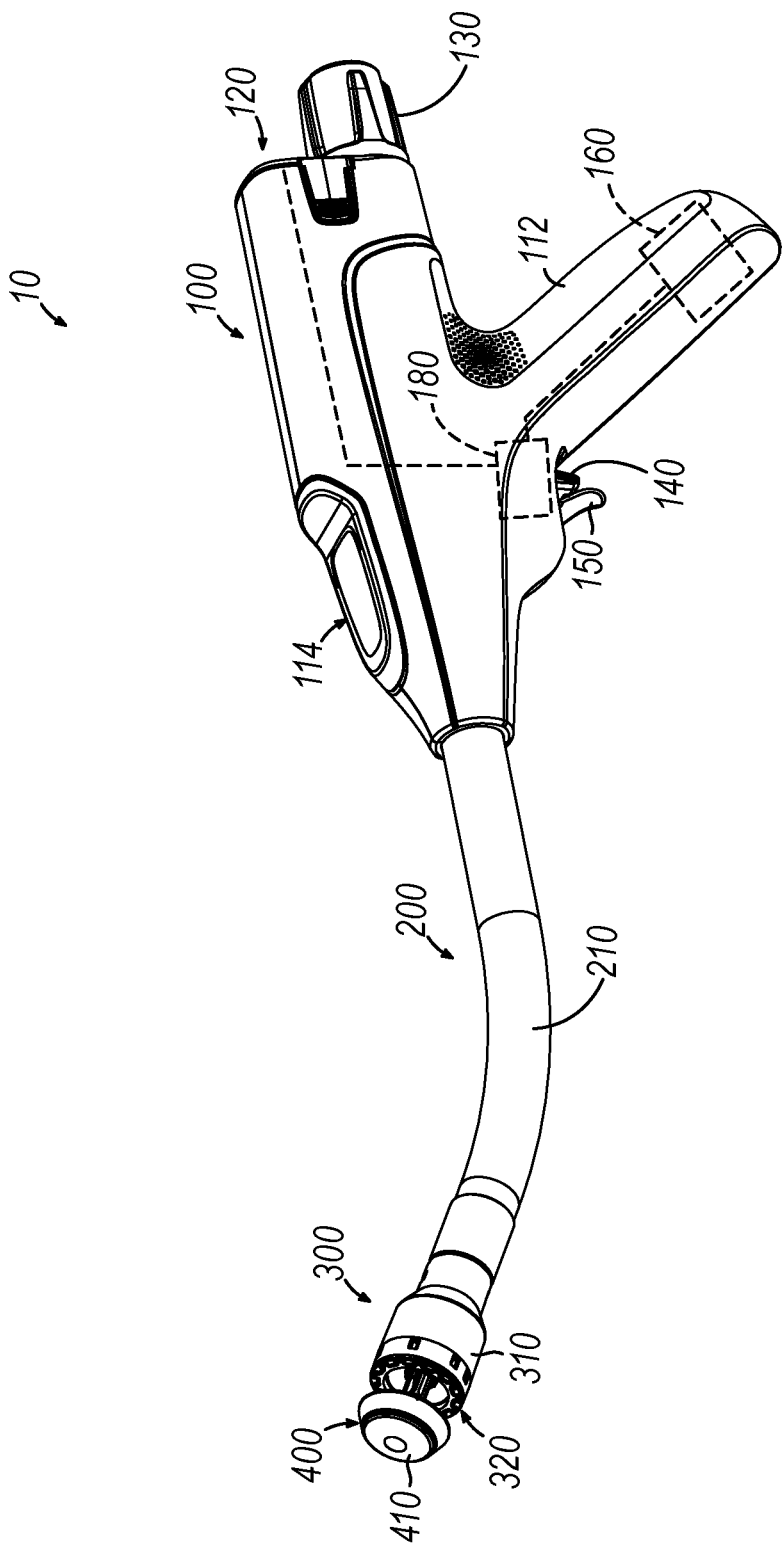
FIG. 1 depicts a perspective view of an exemplary circular surgical stapler that includes a handle assembly, a shaft assembly, and an end effector having a stapling head assembly and an anvil.

The drawings are not intended to be limiting in any way, and it is contemplated that various embodiment of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. OVERVIEW OF EXEMPLARY CIRCULAR SURGICAL STAPLING INSTRUMENT

Figure 2:
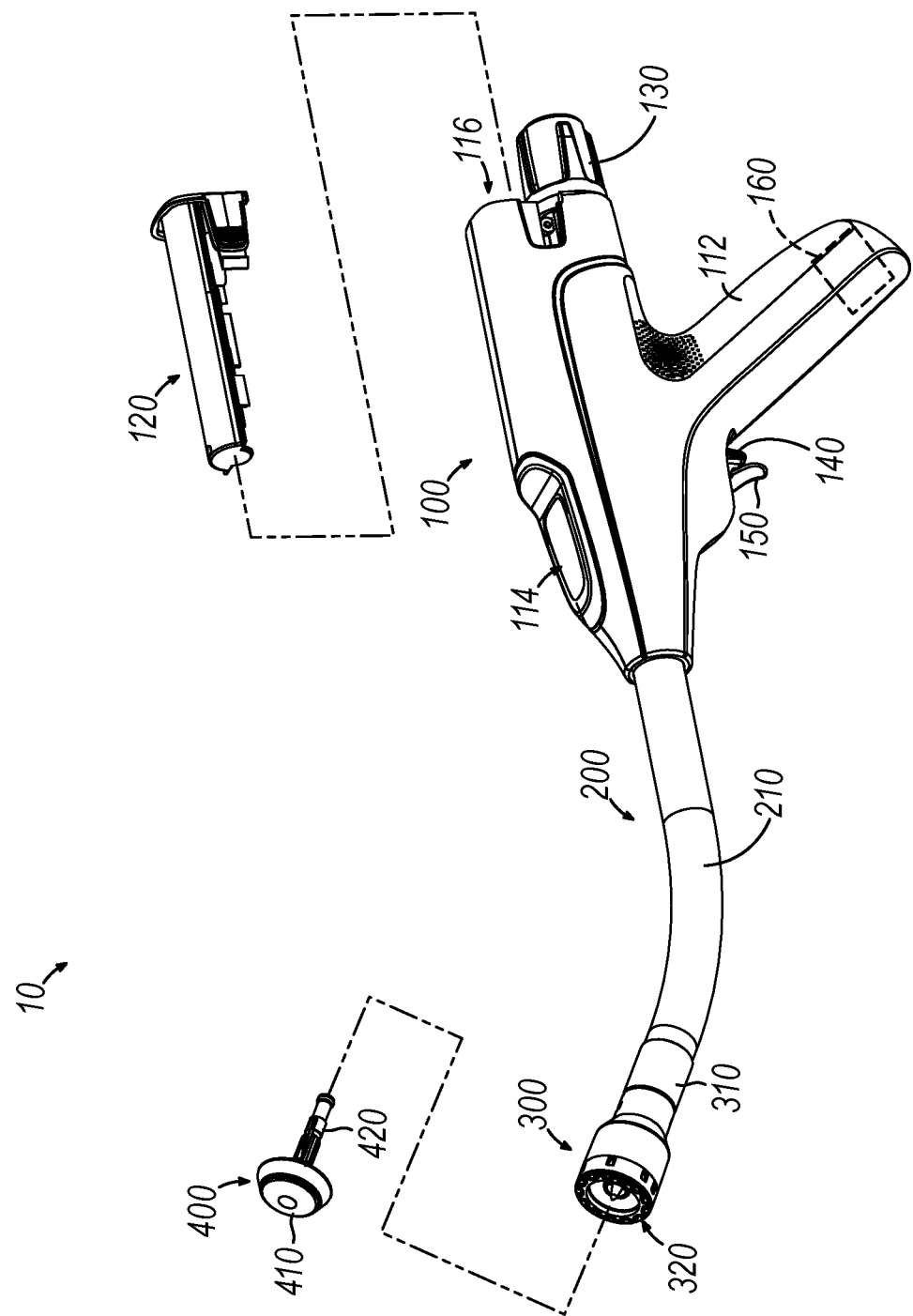
FIG. 2 depicts a perspective view of the circular stapler of FIG. 1, with a battery pack removed from the handle assembly and the anvil separated from the stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly in the form of a handle assembly (100), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A rotatable knob (130) at the proximal end of handle assembly (100) is rotatable to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the clamped tissue.

A. Exemplary Anvil

Figure 3:
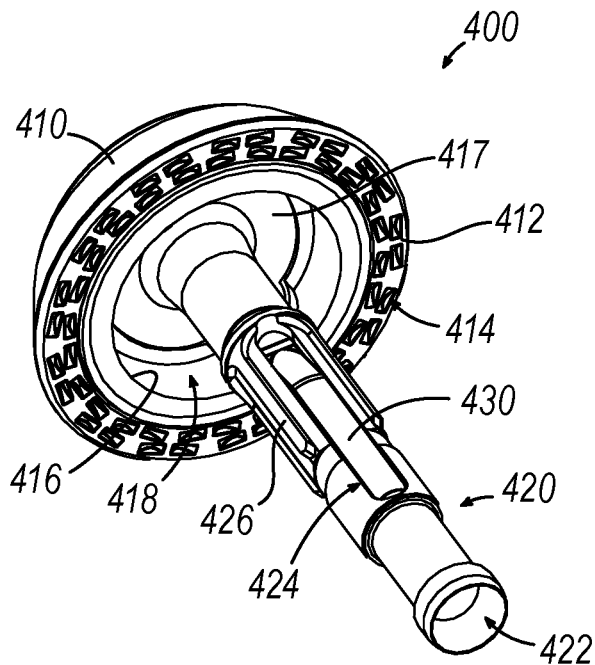
FIG. 3 depicts a perspective view of the anvil of the circular stapler of FIG. 1.

As best seen in FIG. 3, anvil (400) of the present example comprises a head (410) and coupling feature in the form of a shank (420). Head (410) includes a proximal stapling surface (412) that defines a plurality of staple forming pockets (414). Staple forming pockets (414) are arranged in two concentric annular arrays in the present example. Staple forming pockets (414) are configured to deform staples as the staples are driven into staple forming pockets (414). Proximal stapling surface (412) terminates at an inner edge (416), which defines an outer boundary of an annular recess (418) surrounding shank (420). A breakable washer (417) is positioned within annular recess (418), radially inwardly of and adjacent to proximal stapling surface (412), and is configured to provide the user with a tactile and audible indication that a distal firing stroke has been completed, in addition to serving as a cutting board, as described in greater detail below.

Shank (420) defines a bore (422) and includes a pair of pivoting latch members (430). Latch members (430) are positioned within bore (422) such that distal ends (434) are positioned at proximal ends of lateral openings (424), which are formed through sidewall of shank (420). Latch members (430) thus act as retaining clips. This allows anvil (400) to be removably secured to an actuatable closure member in the form of a trocar (330) of stapling head assembly (300), as will be described in greater detail below. Shank (420) of anvil (400) and trocar (330) of stapling head assembly (300) thus cooperate with one another as coupling members.

B. Exemplary Stapling Head Assembly

Figure 4:
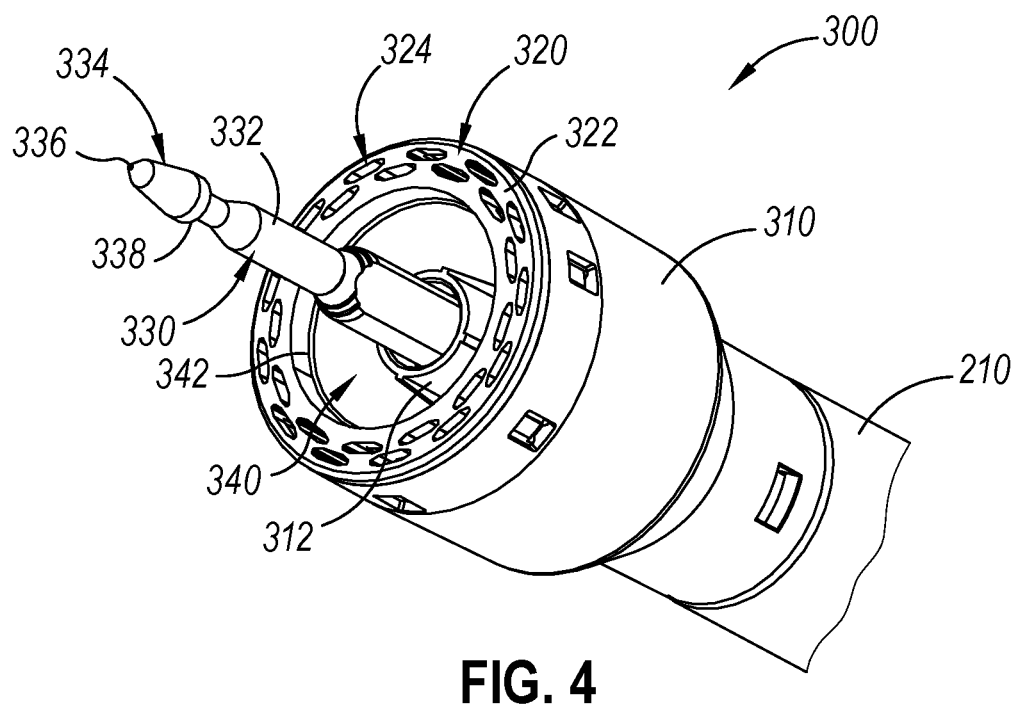
FIG. 4 depicts a perspective view of the stapling head assembly of the circular stapler of FIG. 1.
Figure 5:
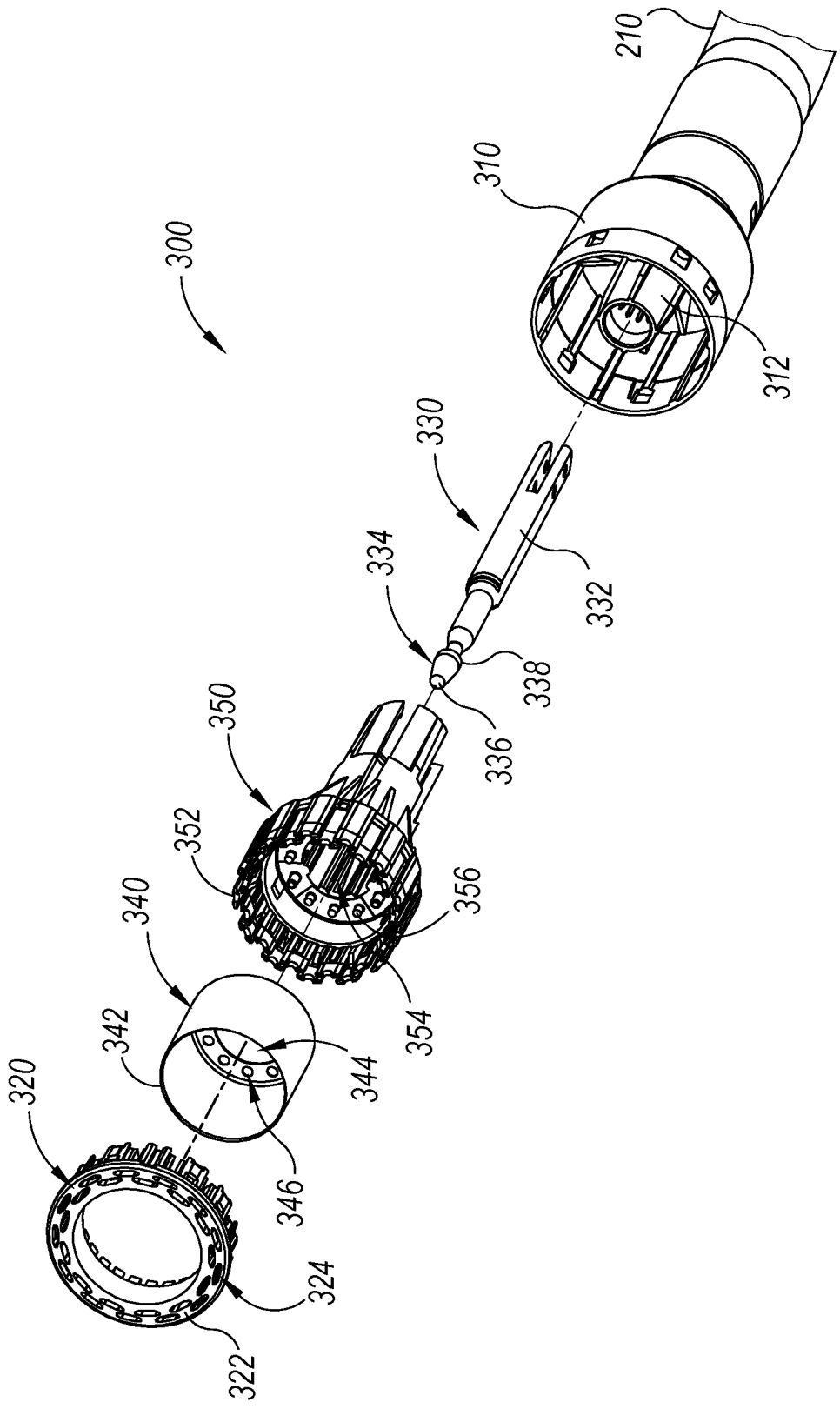
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a tubular body member (310) and a staple driver member (350) slidably housed therein. Body member (310) includes a distally extending cylindraceous inner core member (312) positioned coaxially therein. Body member (310) is fixedly secured to an outer sheath (210) of shaft assembly (200), and body member (310) and outer sheath (210) thus serve together as a mechanical ground for stapling head assembly (300).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and a radially inwardly extending proximal face (338). Head (334) and distal portion of shaft (332) are configured for insertion into bore (422) of anvil (400). Proximal face (338) and latch shelves (436) have complementary positions and configurations such that latch shelves (436) engage proximal face (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. As show best in FIG. 5, staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple distally into a corresponding staple forming pocket (414) when stapling head assembly (300) is actuated (or "fired"). Staple driver member (350) also defines a bore (354) that is configured to coaxially and slidably receive core member (312) of body member (310). An annular array of studs (356) project distally from a distally presented surface surrounding bore (354).

A cylindraceous knife member (340) is coaxially positioned within a distally-opening central recess of staple driver member (350) that communicates with bore (354). Knife member (340) includes a distally presented, sharp circular cutting edge (342). Knife member (340) is sized such that knife member (340) defines an outer diameter that is just smaller than the diameter defined by the radially inner-most surfaces of inner annular array of staple drivers (352). Knife member (340) also defines a central opening that is configured to coaxially receive core member (312) of body member (310). An annular array of openings (346) formed in knife member (340) is configured to mate with annular array of studs (356) of staple driver member (350), such that knife member (340) is fixedly secured to staple driver member (350) via studs (356) and openings (346).

An annular deck member (320) is fixedly secured to a distal end of body member (310). Deck member (320) includes a distally presented stapling surface in the form of a deck surface (322) having two concentric annular arrays of staple openings (324). Staple openings (324) are arranged to align with the arrangement of staple drivers (352) of staple driver member (350) and staple forming pockets (414) of anvil (400) described above. Each staple opening (324) is configured to slidably receive and provide a pathway for a corresponding staple driver (352) to drive a corresponding staple distally through deck member (320) and into a corresponding staple forming pocket (414) when stapling head assembly (300) is actuated. As best seen in FIG. 4, deck member (320) has a central opening that defines an inner diameter that is just slightly larger than outer diameter defined by knife member (340). Deck member (320) is thus configured to permit knife member (340) to translate longitudinally through central opening concurrently with longitudinal translation of staple driver member (350). In particular, knife member (340) is configured to actuate relative to deck member (320) between a proximal retracted position and a distal extended position, where cutting edge (342) is proximal to deck surface (322) in the proximal retracted position and distal to deck surface (322) in the distal extended position.

C. Exemplary Shaft Assembly

Figure 6:
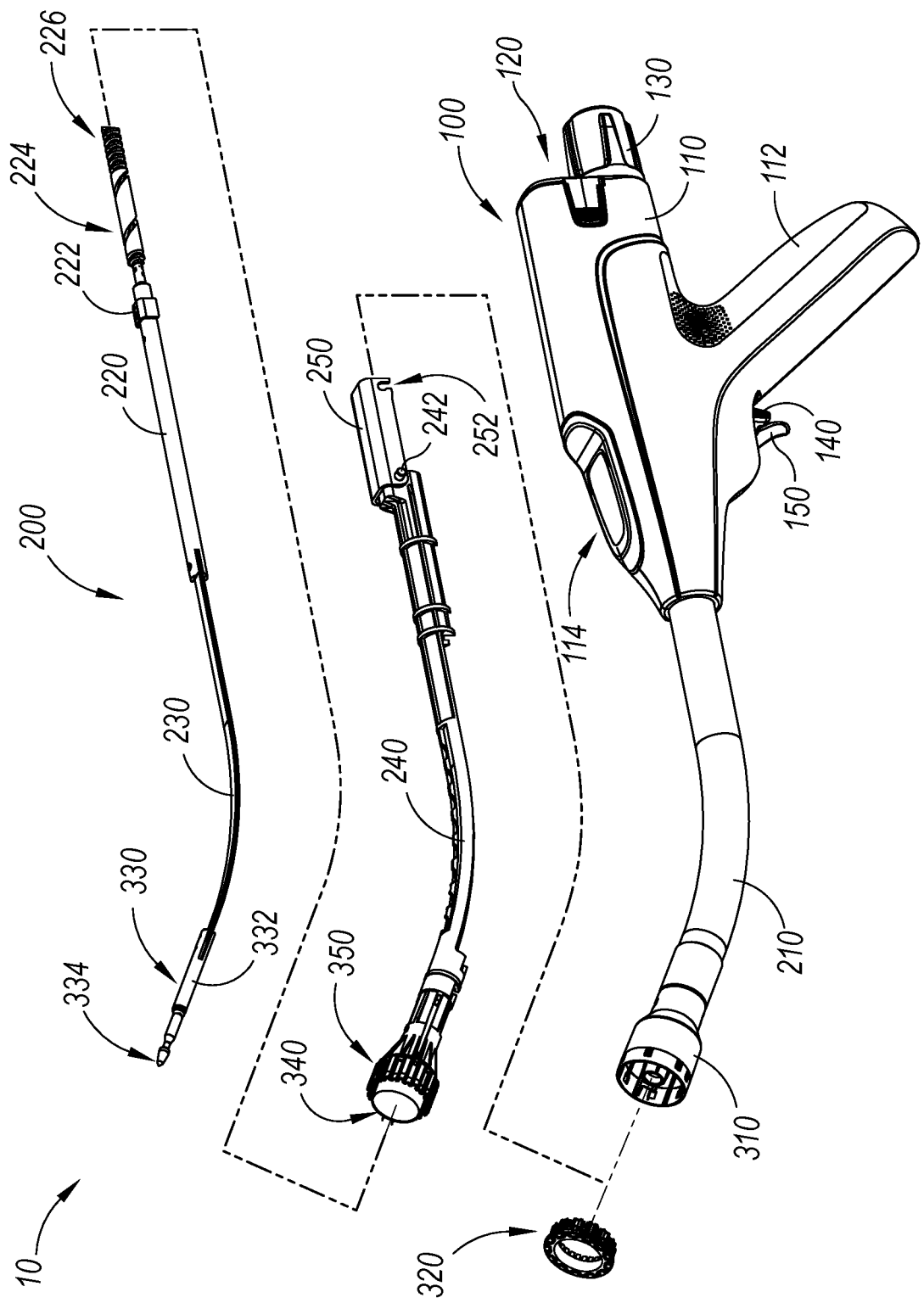
FIG. 6 depicts an exploded perspective view of the circular stapler of FIG. 1, with portions of the shaft assembly shown separated from each other.

FIG. 6 shows various components of shaft assembly (200), which operatively couple components of stapling head assembly (300) with components of handle assembly (100). In particular, and as noted above, shaft assembly (200) includes an outer sheath (210) that extends between handle assembly (100) and body member (310) and includes a medial portion that extends along a curved path.

Shaft assembly (200) further includes a trocar actuation rod (220) having a proximal end operatively coupled with rotatable knob (130) and a distal end coupled with a flexible trocar actuation band assembly (230), the assembly of which is slidably housed within outer sheath (210). The distal end of trocar actuation band assembly (230) is fixedly secured to the proximal end of trocar shaft (332), such that trocar (330) will translate longitudinally relative to outer sheath (210) in response to translation of trocar actuation band assembly (230) and trocar actuation rod (220) relative to outer sheath (210), which occurs in response to rotation of rotatable knob (130). A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a section of coarse helical threading (224) and a section of fine helical threading (226) proximal to coarse helical threading (224), which are configured to control a rate of longitudinal advancement of trocar actuation rod (220), as described in greater detail below.

Shaft assembly (200) further includes a stapling head assembly driver (240) that is slidably housed within outer sheath (210) and about the combination of trocar actuation rod (220) and trocar actuation band assembly (230). Stapling head assembly driver (240) includes a distal end that is fixedly secured to proximal end of staple driver member (350), a proximal end secured to a drive bracket (250) via a pin (242), and a flexible section disposed therebetween. It should therefore be understood that staple driver member (350) will translate longitudinally relative to outer sheath (210) in response to translation of stapling head assembly driver (240) and drive bracket (250) relative to outer sheath (210).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and releasably receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140), a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, and then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) proximally toward stapling head assembly (300); and in a second angular direction (e.g., counterclockwise) to extent anvil (400) distally away from stapling head assembly (300). Knob (130) may thus be used to adjust a gap distance (d) between opposing stapling surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300) to staple and cut tissue clamped between anvil (400) and stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) is operable to actuate a switch of motor activation module (180) (FIG. 1) when firing trigger (150) is pivoted proximally to a fired position. Motor activation module (180) is in communication with battery pack (120) and motor (160), such that motor activation module (180) is configured to provide activation of motor (160) with electrical power from battery pack (120) in response to firing trigger (150) actuating switch of motor activation module (180). Thus, motor (160) will be activated when firing trigger (150) is pivoted. This activation of motor (160) will actuate stapling head assembly (300) via drive bracket (250), as described in greater detail below.

E. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, colon, or other portions of the patient's digestive tract, or any other tubular anatomical structures.

Figure 7A:
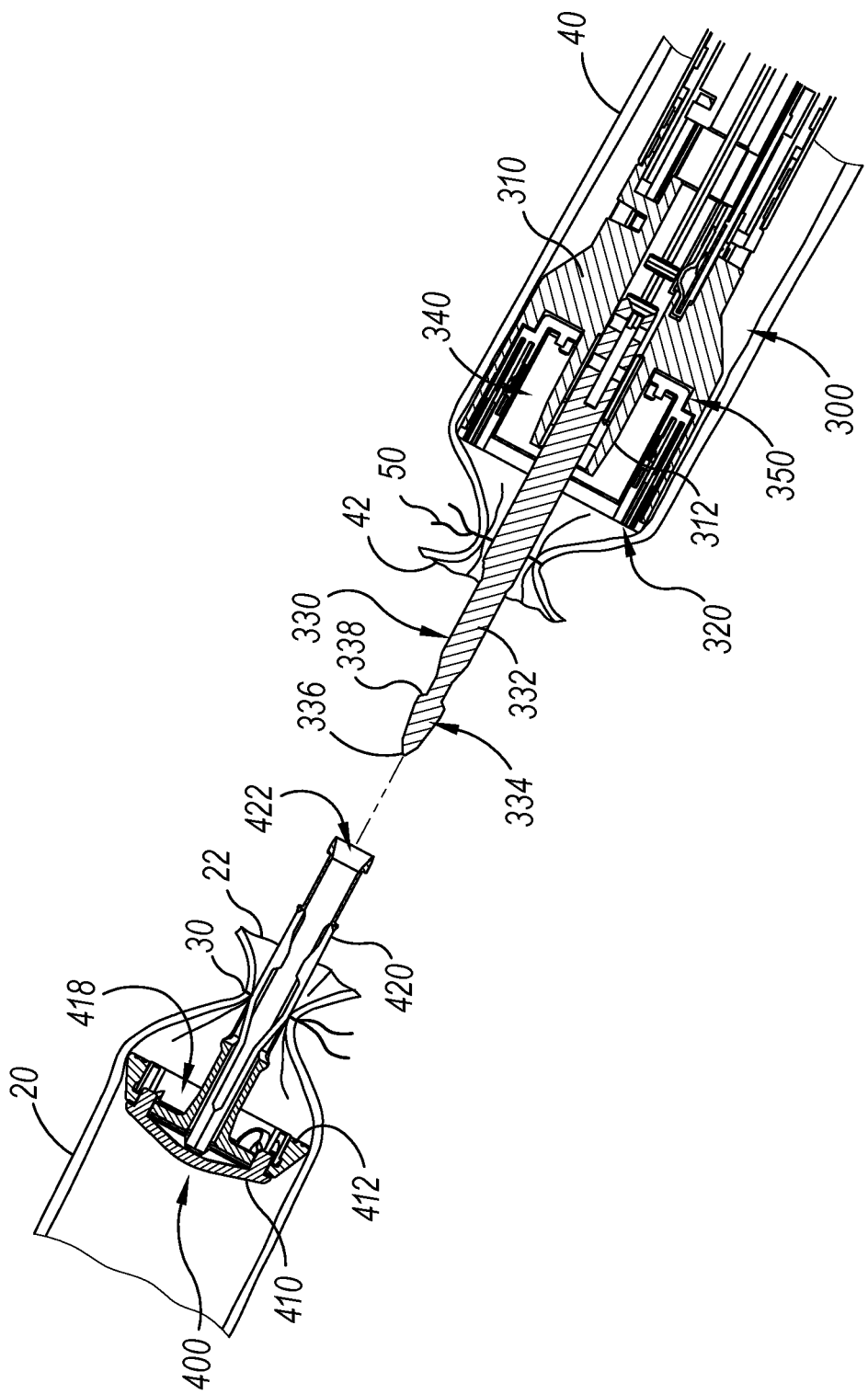
FIG. 7A depicts a cross-sectional side view of the anvil of FIG. 3 positioned within a first section of a digestive tract and the stapling head assembly of FIG. 4 positioned within a separate second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). Anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). Stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at distal end of tubular anatomical structure (40).

Figure 7B:
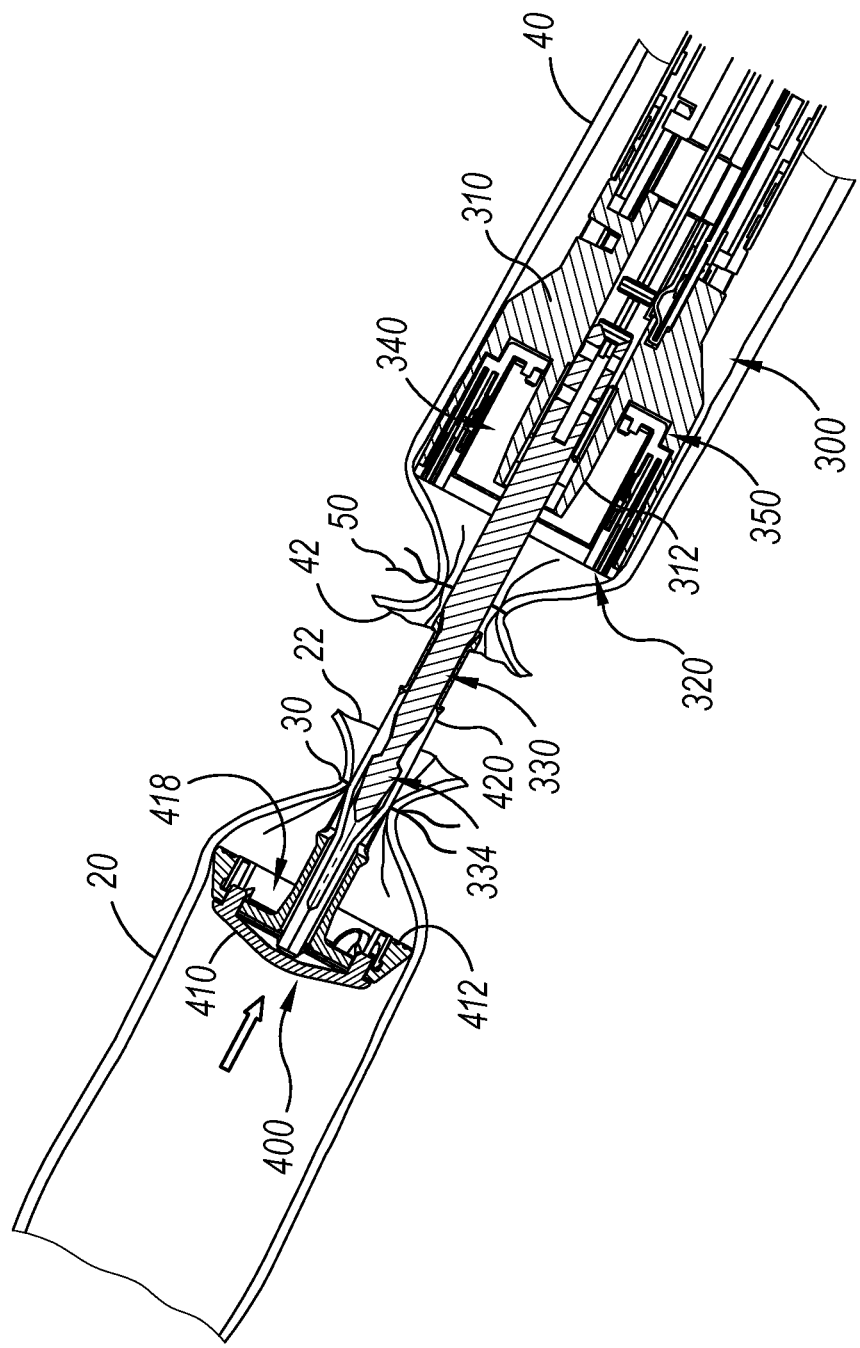
FIG. 7B depicts a cross-sectional side view of the anvil of FIG. 3 positioned within the first section of the digestive tract and the stapling head assembly of FIG. 4 positioned within the separate second section of the digestive tract, with the anvil secured to the stapling head assembly.
Figure 7C:
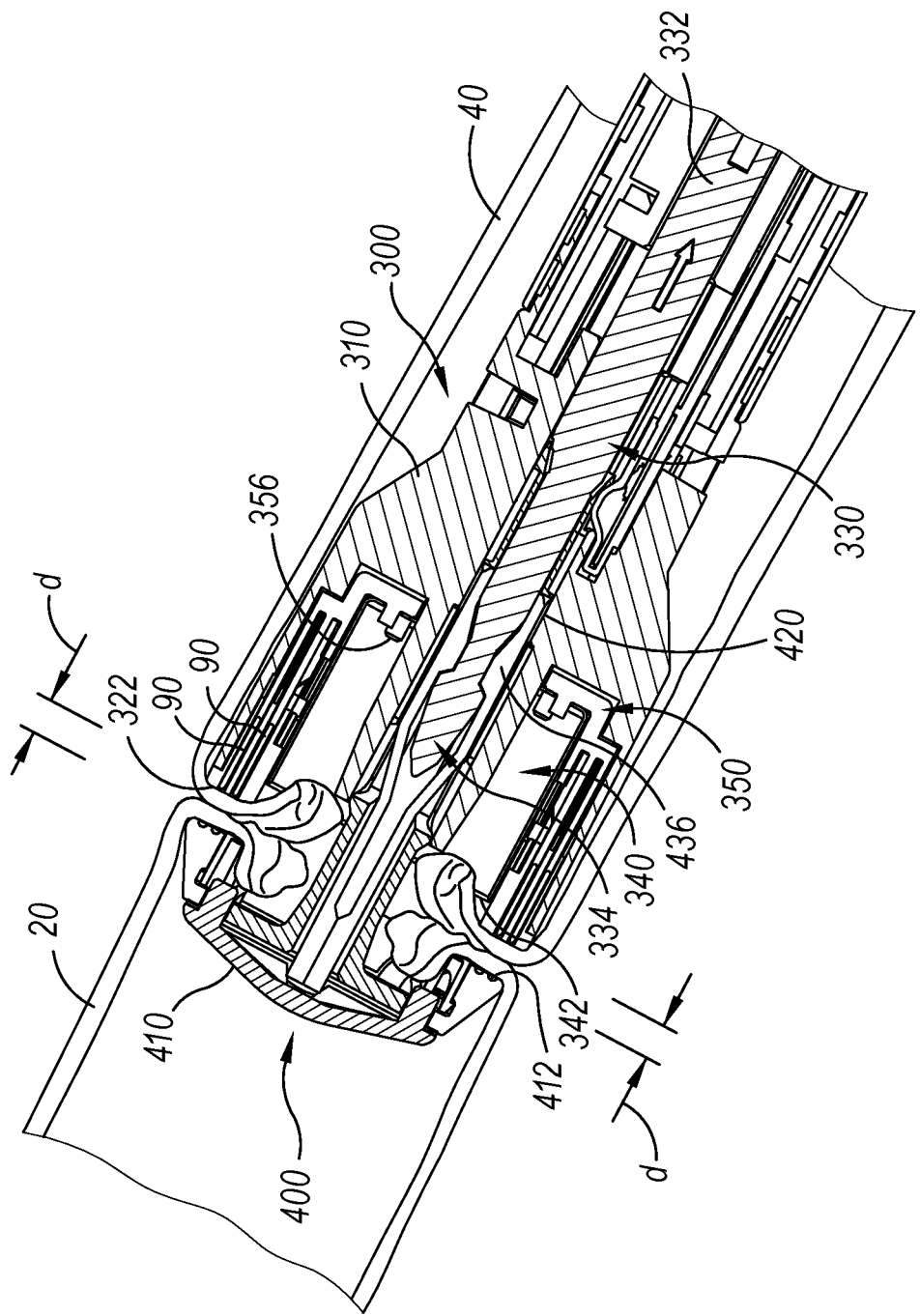
FIG. 7C depicts a cross-sectional side view of the anvil of FIG. 3 positioned within the first section of the digestive tract and the stapling head assembly of FIG. 4 positioned within the separate second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) of anvil (400) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (not shown) within user interface feature (114) of handle assembly (100) to determine whether the gap distance (d) between opposing surfaces (412, 322) of anvil (400) and stapling head assembly (300) is appropriate; and make any necessary adjustments via knob (130).

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing firing trigger (150) to actuate switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally together, as shown in FIG. 7D.

As knife member (340) translates distally, cutting edge (342) of knife member (340) cuts excess tissue that is positioned within annular recess (418) of anvil (400) and interior of knife member (340). In doing so, cutting edge (342) cuts the tissue against a proximal face of breakable washer (417) positioned within annular recess (418) of anvil (400), such that the proximal face of washer (417) functions as a cutting board. As knife member (340) reaches a fully extended state at the distal end of its cutting stroke, cutting edge (342) cuts through the proximal face of washer (417) and thereby breaks away an annular inner portion of washer (417), which can later be removed along with the severed excess tissue. This severing of washer (417) with knife member (340) generates an audible and tactile indication for the operator that the firing stroke has completed.

Figure 7D:
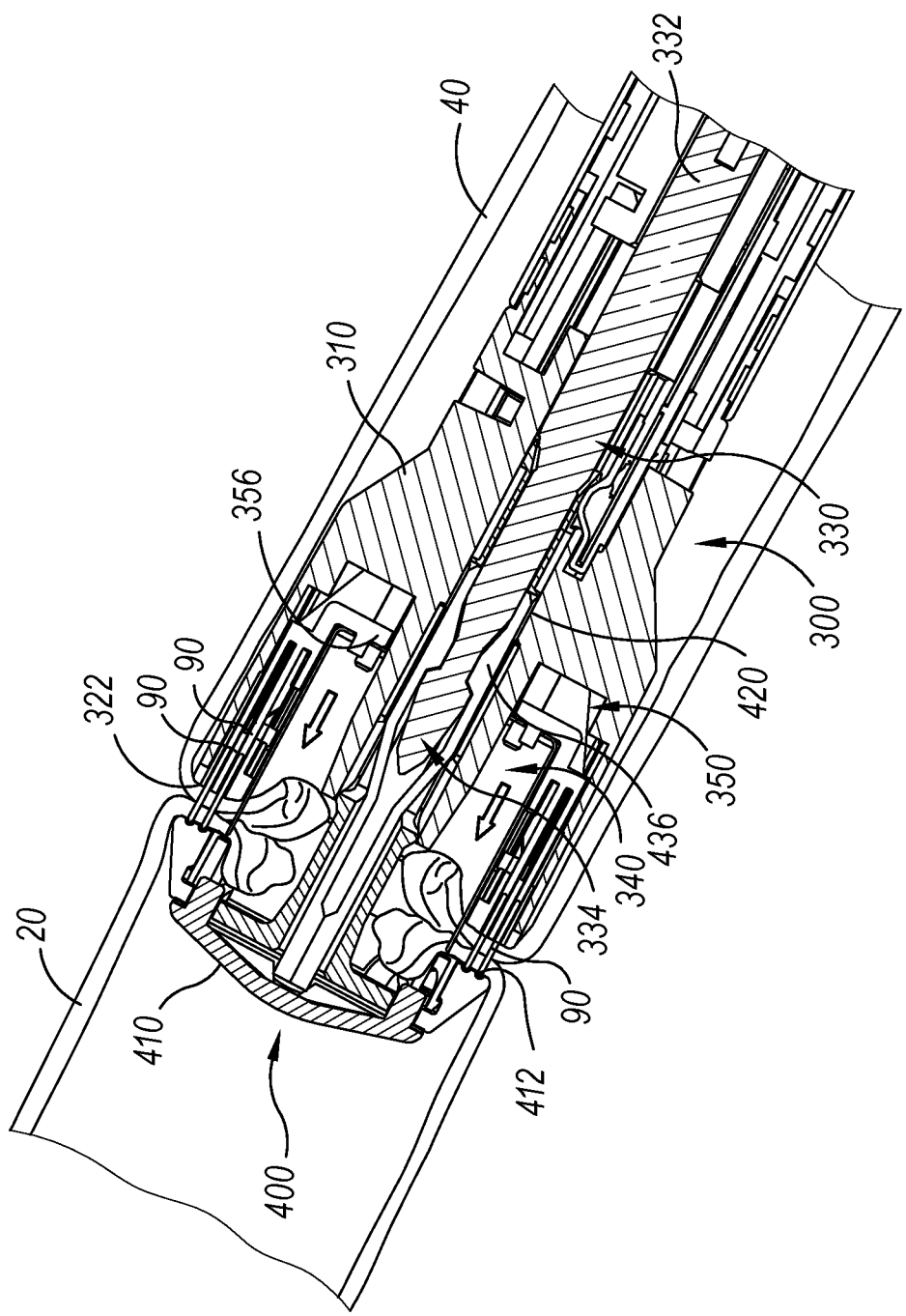
FIG. 7D depicts a cross-sectional side view of the anvil of FIG. 3 positioned within the first section of the digestive tract and the stapling head assembly of FIG. 4 positioned within the second section of the digestive tract, with the stapling head assembly actuated to sever and staple the clamped tissue and thereby joining the first and second sections of the digestive tract.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
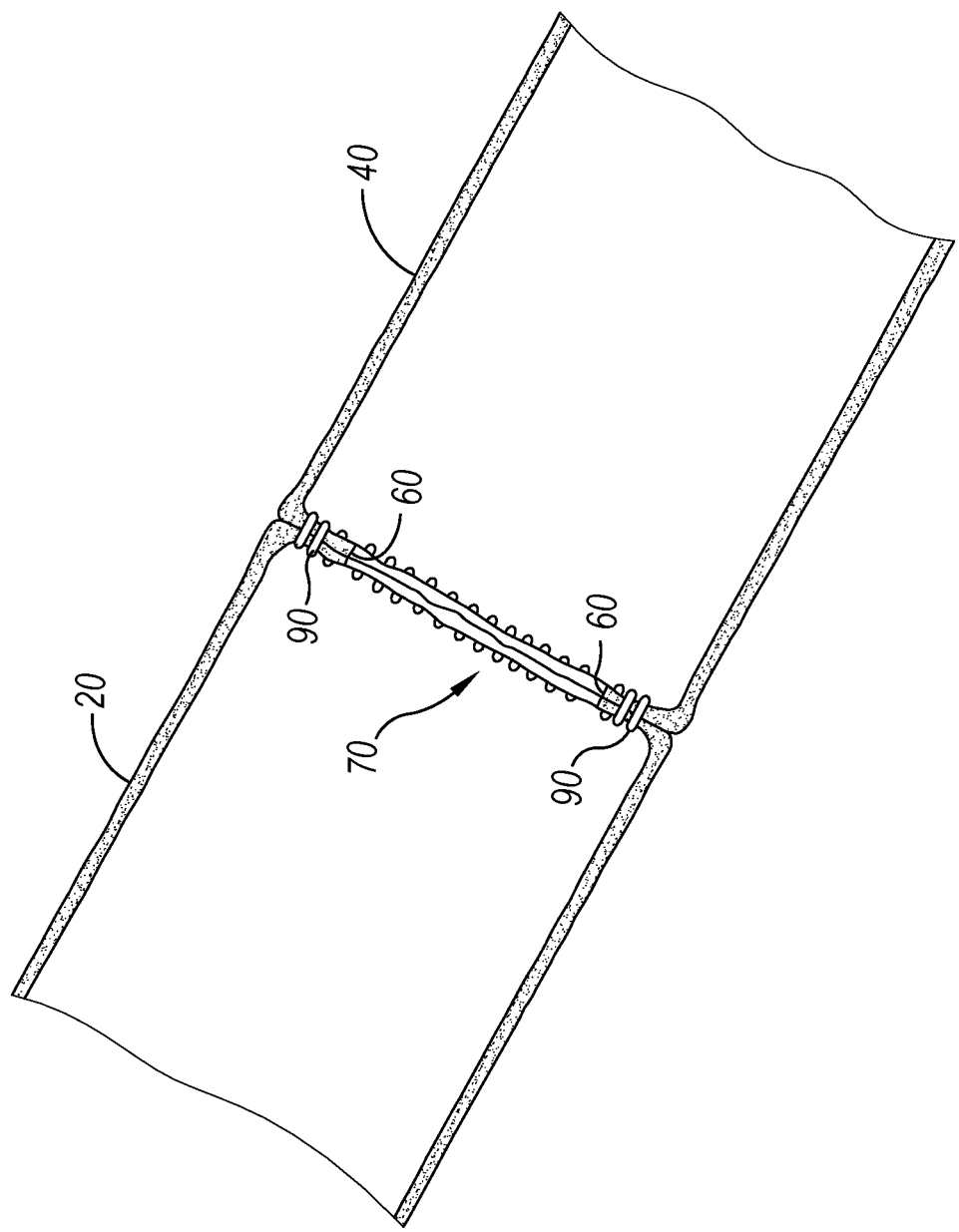
FIG. 7E depicts a cross-sectional side view of the first and second sections of the digestive tract of FIG. 7A joined together at an end-to-end anastomosis formed with the circular stapler of FIG. 1.

After the operator has actuated (or "fired") stapling head assembly (300) as shown in FIG. 7D, the operator rotates knob (130) to drive anvil (400) distally away from stapling head assembly (300), thereby increasing the gap distance (d) to facilitate release of the tissue between surfaces (412, 322). The operator then removes instrument (10) from the patient, with anvil (400) still secured to trocar (330). With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. EXEMPLARY END EFFECTORS HAVING BREAKABLE WASHER WITH TISSUE GRIPPING FEATURES

As noted above, washer (417) is broken by knife member (340) when knife member (340) completes a full distal range of motion from the position shown in FIG. 7C to the position shown in FIG. 7D. It may be desirable for the tissue to be fully transected by knife member (340) prior to washer (417) breaking. However, in some instances, washer (417) may insufficiently stabilize the tissue as cutting edge (342) advances distally through the tissue and washer (417), such that some portions of tissue (referred to as "tags") may translate across anvil surface (412) and the proximal face of washer (417) and get pushed and stretched distally by cutting edge (342) between the broken edges of washer (417) and remain uncut.

Accordingly, in some procedures, it may be desirable to more effectively stabilize the tissue on the proximal face of washer (417), thereby reducing the likelihood that the tissue is pushed into a gap of broken washer (417); and increasing the likelihood that the tissue is fully cut by knife member (340). The exemplary configurations described below incorporate various features that may promote complete cutting of tissue with surgical stapler (10) and/or provide other benefits.

A. Exemplary Anvil Having Breakable Washer with a Rough Feature

Figure 8:
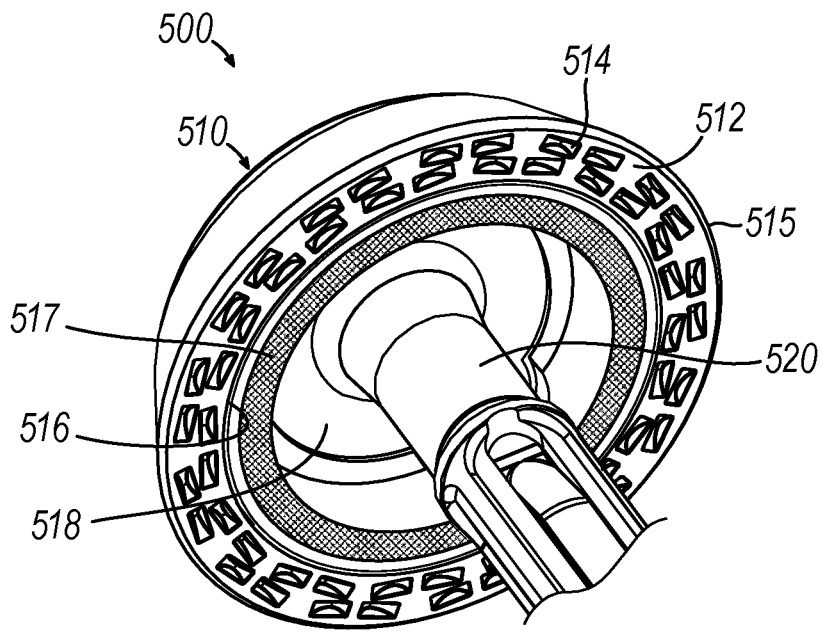
FIG. 8 depicts an enlarged perspective view of a portion of another exemplary anvil for use with the circular stapler of FIG. 1.

FIG. 8 shows a portion of an exemplary anvil (500) configured for use with surgical instrument (10) in place of anvil (400). It will be appreciated that anvil (500) is similar in structure and function to anvil (400) described above except as otherwise described. In particular, and as described in greater detail below, anvil (500) of the present example includes a washer (517) configured to stabilize tissue and promote complete cutting of the tissue when performing the cutting sequence to create an anastomosis between tubular anatomical structures (20, 40) when coupled to stapling head assembly (300).

Similar to anvil (400) described above, anvil (500) includes a head (510) and a shank (520) extending proximally from head (510). Anvil (500) is configured to releasably couple with trocar (330) of stapling head assembly (300). Head (510) has a circular shape similar to an exterior profile of body member (310) of stapling head assembly (300). Circular shape of head (510) defines a proximal stapling surface (512) having a plurality of staple forming pockets (514) similar to staple forming pockets (414) described above. Proximal stapling surface (512) is configured to cooperate with deck surface (322) to clamp and staple tissue. Proximal stapling surface (512) includes radially inner and outer edges (516, 515). Inner edge (516) of proximal stapling surface (512) compliments outer edge (515) resulting in proximal stapling surface (512) having an annular shape. Inner edge (516) defines the shape of an annular recess (518) positioned radially inwardly of and adjacent to proximal stapling surface (512), and at the center of which shank (520) extends proximally.

Anvil (500) further includes a washer (517) seated within annular recess (518), radially inwardly of and adjacent to proximal stapling surface (512), and having a circular shape defined by the shape of annular recess (518) similar to washer (417) described above. Washer (517) differs from washer (417) in that washer (517) is configured to more effectively stabilize tissue when being cut by knife member (340) of stapling head assembly (300) during the cutting sequence of a firing stroke of stapler (10). In some versions, though not shown, washer (517) may have an elongate shape such as oval, or any other non-circular shapes defined by the shape of annular recess.

Figure 9:
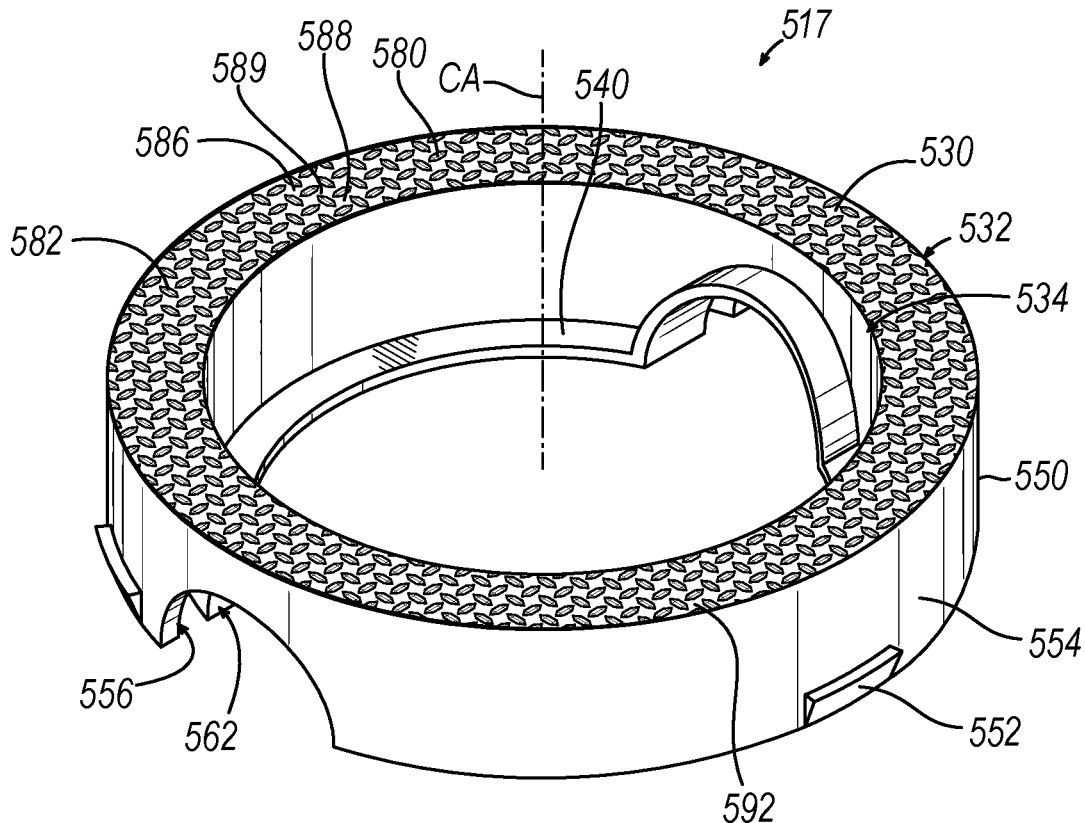
FIG. 9 depicts a perspective view of an exemplary washer of the anvil of FIG. 8, where the washer has a tissue gripping feature in the form of a rough surface.

As best seen in FIG. 9, washer (517) includes an annular shape extending distally along a central axis (CA) from a proximal wall (530) to a flange-like distal wall (540). Proximal wall (530) is transversely positioned relative to central axis (CA). Proximal wall (530) is fixedly secured to a proximal portion of a cylindrical outer wall (550) at an outer edge (532) of proximal wall (530) and fixedly secured to a proximal portion of a cylindrical inner wall (560) at an inner edge (534) of proximal wall (530).

Figure 10:
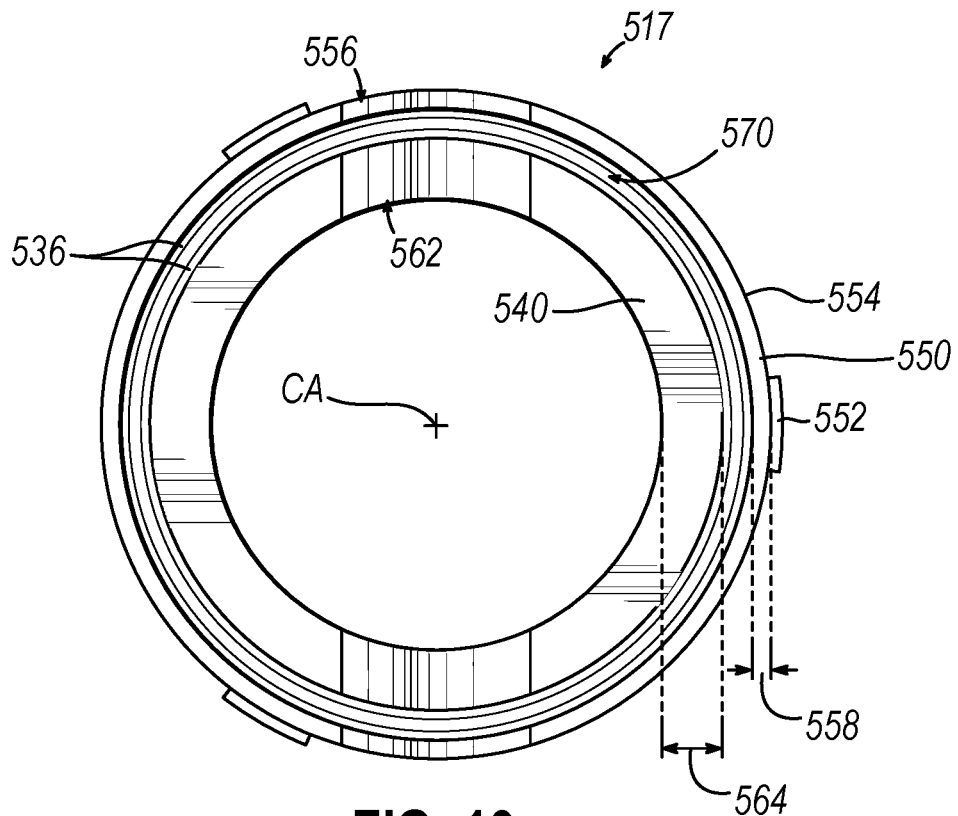
FIG. 10 depicts a plan view of a distal side of the washer of FIG. 9.
Figure 13A:
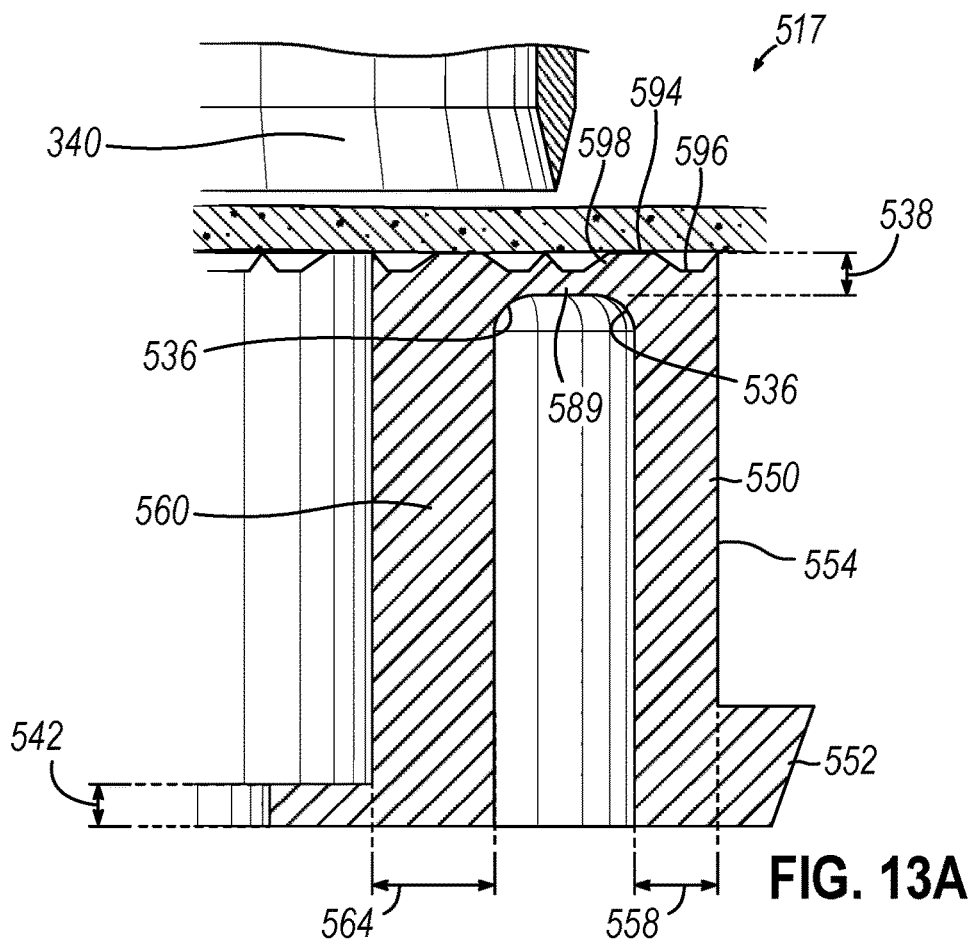
FIG. 13A depicts a partial cross-sectional side view of the washer of FIG. 9, taken along line 13A-13A of FIG. 11, with the knife member in a proximal pre-fired position and with other details of the corresponding end effector being omitted.
Figure 13B:
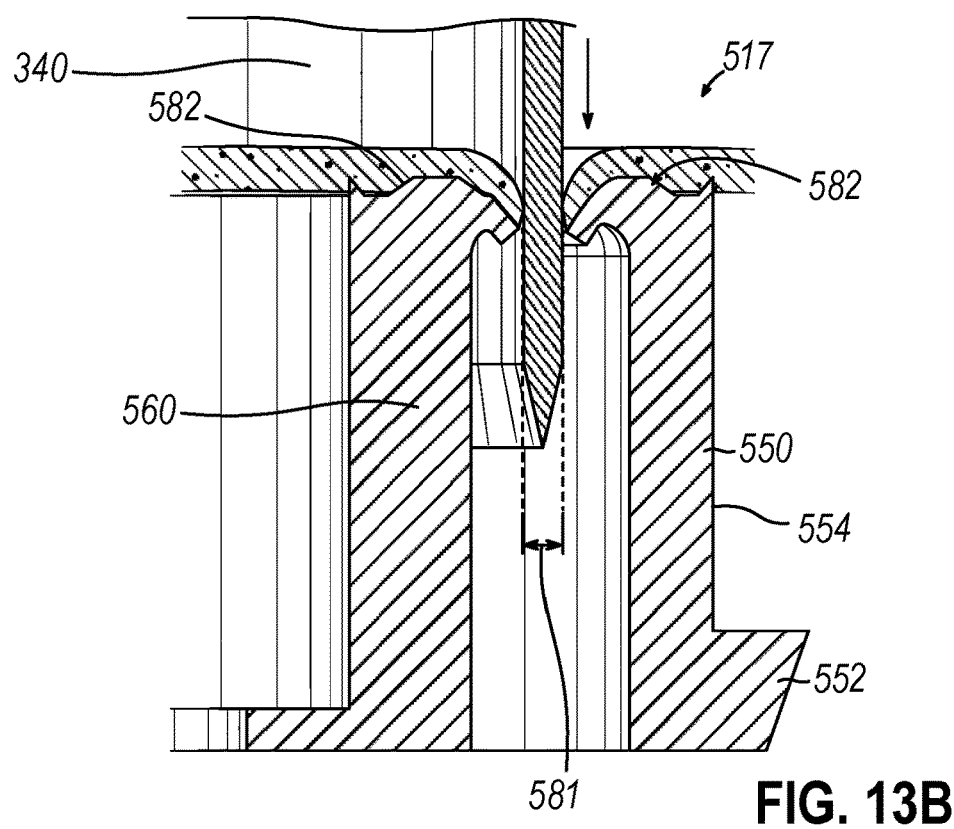
FIG. 13B depicts another partial cross-sectional side view of the washer of FIG. 9, taken along line 13A-13A of FIG. 11, with the knife member in a distal fired position after transecting the washer and tissue.

As best seen in FIG. 10, proximal wall (530), outer wall (550), inner wall (560) and distal wall (540) are integrally formed from a single component. In other versions, proximal wall (530), outer wall (550), and distal wall (540) may be separate components fastened together. As shown in FIGS. 10 and 13A-13B, proximal wall (530) defines an annular web (589) that extends circumferentially along a circumferential center line of proximal wall (530) and thereby radially interconnects the proximal ends of outer wall (550) and inner wall (560). Web (589), also referred to herein as a "central portion" of proximal wall (530), is thinner than surrounding portions of washer (517), thus promoting its severing by cutting edge (342) of knife member (340) at the distal end of a firing stroke. Web (589) is supported by tapered transitions (536) that join web (589) to the inner and outer walls (550, 560). Proximal wall (530), inner wall (560), and outer wall (550) have respective inner surfaces that collectively define a washer recess (570). Washer recess (570) is annular and sized slightly larger than knife member (340) in a radial direction in order to provide clearance between knife member (340) and the inner and outer walls (560, 550). Distal wall (540) is fixedly secured to a distal portion of the inner wall (560) and extends radially inwardly towards central axis (CA), thus defining an inner flange-like structure. Distal wall (540) is configured to mate with a proximal facing surface of anvil head (510) within annular recess (518) to stabilizes washer (517) within annular recess (518).

Figure 11:
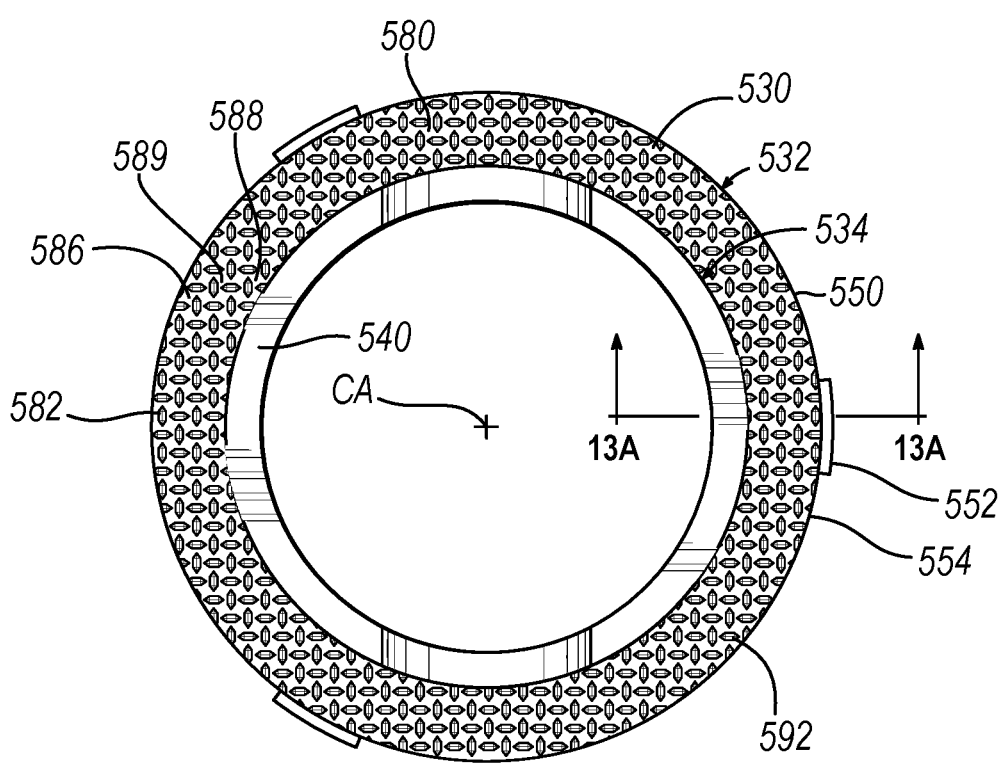
FIG. 11 depicts a plan view of a proximal side of the washer of FIG. 9.

As best seen in FIG. 11, outer wall (550) of washer (517) includes an outer surface (554) having a plurality of retaining features (552) configured to retain washer (517) within annular recess (518) of anvil (500). While three retaining features (552) are shown in the present version, various other quantities of retaining features (552) may be provided in other versions. Each of retaining features (552) may be positioned an equal circumferential distance from other retaining features (552) or an unequal circumferential distance from other retaining features (552). Each retaining feature (522) is configured to mate with a retaining recess (not shown) positioned about the interior of annular recess (518) to retain the washer (517) within the annular recess (518). Outer wall (550) further includes a pair of outer archways (556) defined by a distal portion of outer wall (550). Pair of outer archways (556) is positioned transverse to the central axis (CA). Inner wall (560) includes a pair of inner archways (562) positioned transverse to the central axis (CA) and aligned with the pair of outer archways (556).

Proximal wall (530) includes a proximal face (580) configured to be transected by cutting edge (342) of knife member (340). Proximal face (580) thus faces toward knife member (340) when anvil (500) is secured to trocar (330). Proximal face (580) includes a tissue gripping feature in the form of a rough feature (582) that covers the entire proximal face (580). Gripping feature (582) is integrally formed with the proximal wall (530) so as to define a rough proximally-facing surface, and is formed of a rigid material covering the entire proximal face (580). By way of example only, rough feature (582) may be formed upon the proximal face (580) by mechanically grinding, mechanically cutting, chemically treating, or casting within a mold.

In other versions, gripping feature (582) may cover only a portion of proximal face (580). For example, gripping feature (582) may cover a radially outer portion (586) of the proximal face (580) and a radially inner portion (588) of the proximal face (580), and be omitted from an annular central portion defined by web (589) between radially outer and inner portions (586, 588). Such a configuration is exhibited by washer (617) of FIG. 14 having a smooth surface (690) along its annular central portion (689).

In yet other versions, gripping feature (582) may be constructed of a flexible material (not shown) chemically applied or mechanically fastened to proximal face (580). Flexible material is configured to provide flexibility so that a large range of tissue thickness that may be transected.

Figure 12:
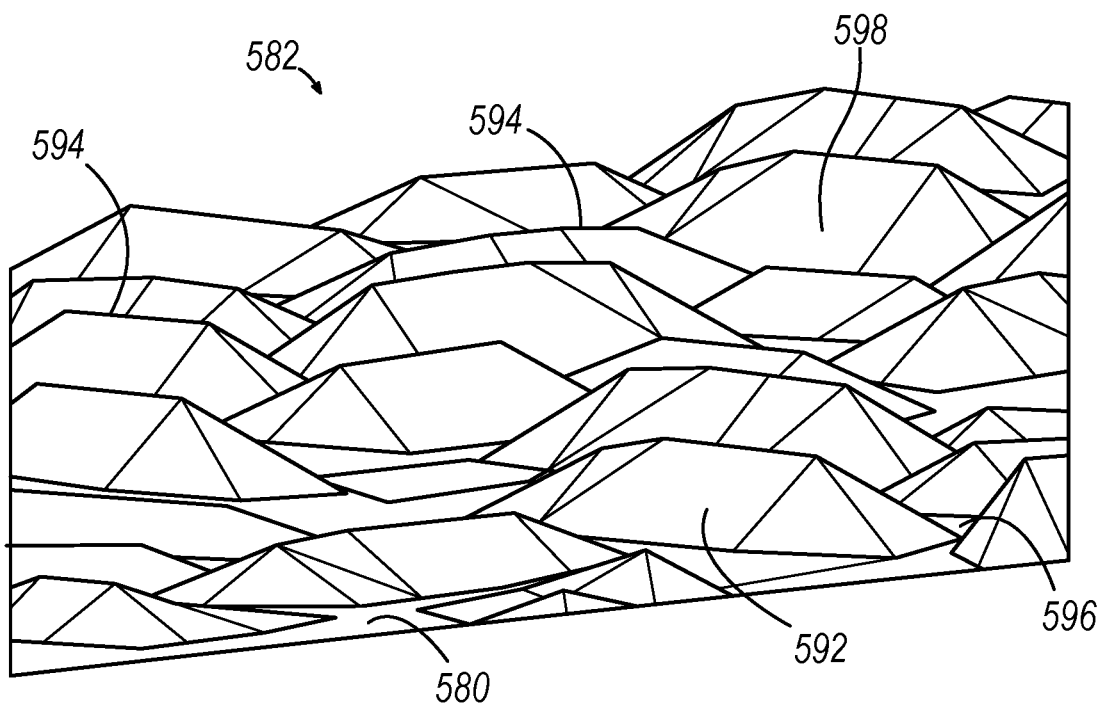
FIG. 12 depicts an enlarged perspective view of a proximal face of the washer of FIG. 9.

As best seen in FIG. 12, rough feature (582) includes a plurality of proximally tapered projections (592) extending proximally from proximal face (580). In the present version, each projection (592) is arranged in a symmetrical pattern in which each projection (592) is spaced a set distance relative to other projections (592) or a set angular orientation relative to other projections (592) about the central axis (CA). Various other patterns and shapes of projections (592) may be provided in other versions of washer (517). Projections (592) are configured to grip portions of tissue compressed around projections (592) and thereby stabilize and inhibit tissue from translating across proximal face (580) and anvil surface (512) (see FIG. 8) when surgical instrument (10) is fired.

As best seen in FIG. 12, rough feature (582) may also have a plurality of irregular projections (598) extending proximally from proximal face (580) (i.e., toward knife member (340) and tissue). Each irregular projection (598) may include different shapes extending distally at different heights and angles relative to other irregular projections (598). Irregular projections (598) may be arranged in a non-symmetrical pattern and may include sharp edges and facets configured to shallowly pierce tissue to further maintain tissue stability. Each irregular projection (598) has a peak (594) farthest from the proximal face (580) spaced and valley (596) located between two peaks (594). Valley (596) may be located on the proximal face (580) or may be spaced apart from the proximal face (580).

As best seen in FIGS. 9-11, inner wall (560) includes a first thickness (564), outer wall includes a second thickness (558), distal wall (540) includes a third thickness (542), and web (589) of proximal wall (530) includes a fourth thickness (538). First thickness (564) is greater than second thickness (558), second thickness is greater than third thickness (542), and third thickness (542) is greater than fourth thickness (538). Fourth thickness (538) is configured to be easily cut by cutting edge (342) and therefore is desirable to be smaller than the other thicknesses (564, 558, 542). An easily cut proximal wall (530) minimizes force to fire. First thickness (564) and second thickness may be any size configured to provide rigidity to proximal wall (530) so that inner and outer walls (560, 550) do not deflect or break when engaged by cutting edge (342). It should be noted that the thicknesses of proximal wall (530), distal wall (540), inner wall (560), and outer wall (550) are merely illustrative examples and may be any thickness capable of stabilizing washer (571) with minimal deflection so a clean cut may be created through tissue with knife member (340).

FIG. 13A schematically shows stapling head assembly (300) coupled with anvil (500) with portions omitted for clarity. Knife member (340) is located in a proximal position relative to washer (517) with cutting edge (342) concentrically aligned with web (589). In the proximal position, deck member (322) and proximal stapling surface (512) have compressed tissue therebetween providing some distal pressure upon the tissue (see FIG. 7C). Rough feature (582) lightly engages tissue to stabilize tissue on proximal face (580) before knife member (340) is translated distally.

Knife member (340) is translated distally until cutting edge (342) engages tissue, providing distal pressure on tissue between cutting edge (342) and web (589). Additionally, proximal stapling surface (512) and rough feature (582) further engages tissue to stabilize tissue from stretching or moving transversely by projections (598) "biting" into tissue. Once cutting edge (342) engages tissue, washer (517) acts as a cutting board while cutting edge (342) cuts through tissue in an abrupt guillotine-type cutting action severing tissue along the circumferential centerline of web (589).

FIG. 13B schematically shows the stapling head assembly (300) and anvil (500) of FIG. 13A with knife member (340) in the distal position. In the distal position, knife member (340) has translated distally and has transected web (589) of washer (517), creating a gap (581) in web (589). Washer (517) breaks, producing an audible and/or tactile feedback to the user to indicate completion of tissue cutting and stapling. As knife member (340) continues to translate distally beyond web (589) between inner and outer walls (560, 550), rough feature (582) continues to engage and stabilize tissue in a radial direction of washer (517), which inhibits the cutting edge (342) from stretching and/or dragging tissue distally through gap (581), ensuring that tissue is fully severed.

B. Exemplary Anvil Having Breakable Washer with Raised Nubs

Figure 14:
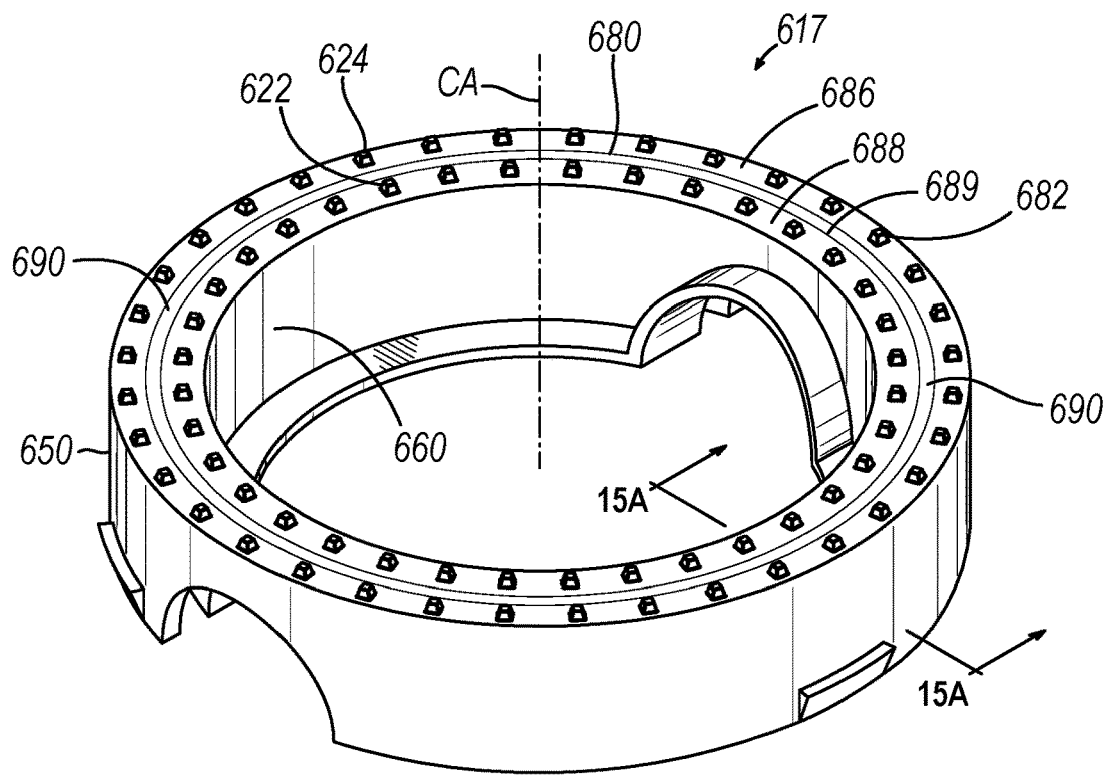
FIG. 14 depicts a perspective view of another exemplary washer for use with the anvil of FIG. 8, where the washer has a tissue gripping feature in the form of a plurality of raised nubs.

FIG. 14 shows another exemplary washer (617) for use with anvil (500) to be incorporated into surgical instrument (10). It will be appreciated that washer (617) is similar in structure and function to washer (517) described above except as otherwise described. In particular, and as described in greater detail below, washer (617) of the present example includes a tissue gripping feature in the form of a plurality of raised nubs (682) on a proximal face (680). Proximal face (680) would face toward knife member (340) when a version of anvil (500) incorporating washer (617) is secured to trocar (330).

Each of raised nubs (682) has a shape of a truncated pyramid. Raised nubs (682) may be other suitable shapes such as a pyramid, a cone, a truncate cone, a cylinder, a square, a rectangle, a partial sphere, a partial ellipse, or any shape known in the art to grab tissue. Plurality of raised nubs (682) is arranged in inner and outer rows (622, 624) in a symmetrical pattern. Inner row (622) is spaced a first radial distance from the central axis (CA) of washer (617) and arranged along a radially inner annular portion (688) of proximal face (680). Outer row (624) is spaced a second radial distance from central axis (CA) and arranged along a radially outer annular portion (686) of proximal face (680). Second distance is greater than first distance. Each of raised nubs (682) of inner row (622) is aligned with one of the raised nubs (682) of outer row (624) at an angle relative to central axis (CA) of washer (617). Proximal face (680) further includes a smooth surface (690) located on a central portion (689) between radially outer and inner portions (686, 688). Smooth surface (690) is configured to allow cutting edge (342) of knife member (340) to evenly engage tissue along a circumferential centerline of central portion (689).

Figures 15A, 15B:
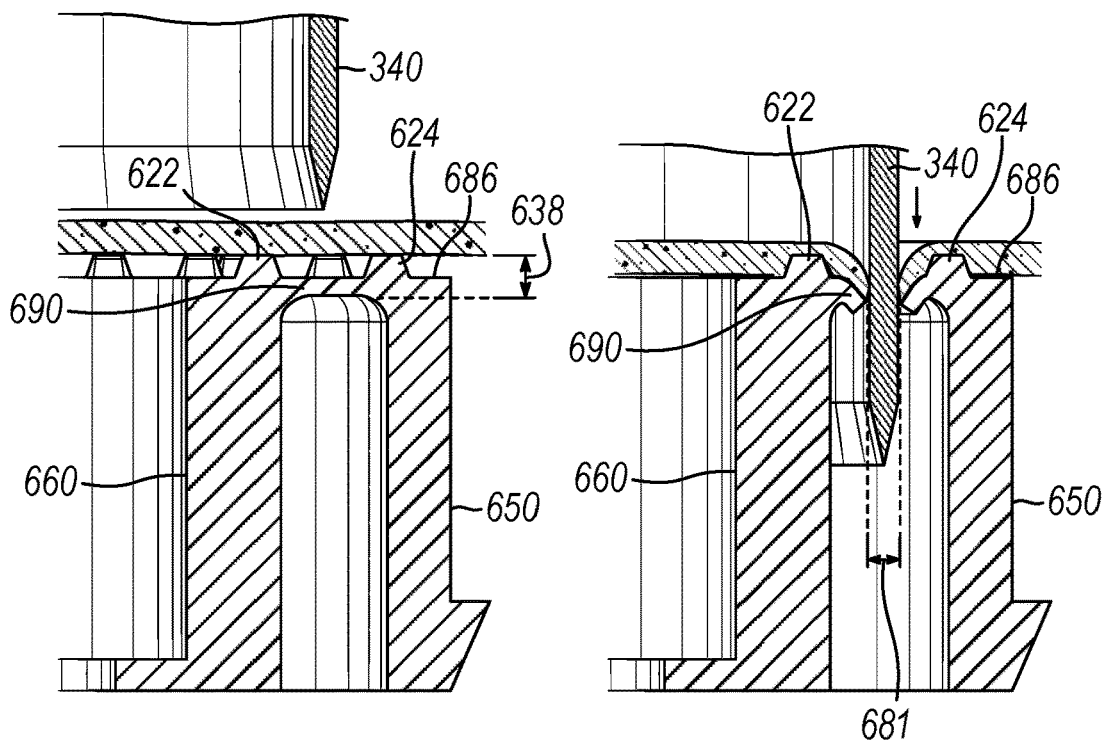
FIG. 15A depicts a partial cross-sectional side view of the washer of FIG. 13, taken along line 15A-15A of FIG. 14, with the knife member in a proximal pre-fired position and with other features of the corresponding end effector being omitted.
FIG. 15B depicts another partial cross-sectional side view of the washer of FIG. 13, taken along line 15A-15A of FIG. 14, with the knife member in a distal fired position after transecting the washer and tissue.

FIG. 15A schematically shows stapling head assembly (300) coupled with anvil (500) including washer (617) with portions omitted for clarity. Knife member (340) is located in a proximal position relative to washer (617) with cutting edge (342) concentrically aligned with central portion (689). Deck member (322) and proximal stapling surface (512) have compressed tissue therebetween providing some distal pressure upon the tissue (see FIG. 7C). Plurality of raised nubs (682) lightly engages tissue to stabilize tissue on proximal face (680) before knife member (340) is translated distally.

Knife member (340) is translated distally until cutting edge (342) engages tissue providing additional distal pressure on tissue between cutting edge (342) and central portion (689). Distal pressure forces tissue around plurality of raised nubs (682), which further engage tissue to stabilize tissue from stretching or moving transversely. Once cutting edge (342) engages tissue, washer (717) acts as a cutting board while cutting edge (342) cuts through tissue in an abrupt guillotine-type cutting action severing tissue around the circumference of cutting edge (342).

FIG. 15B schematically shows the stapling head assembly (300) and anvil (500) of FIG. 15A. Knife member (340) has translated distally from the proximal position to a distal position and has transected the central portion (689) creating a gap (681) in central portion (689). Washer (617) breaks producing an audible and/or tactile feedback to the user to indicate completion of tissue cutting and stapling. As knife member (340) continues to translate distally beyond the proximal wall between inner and outer walls (660, 650), raised nubs (682) continue to engage and stabilize tissue in a radial direction of washer (617), which inhibits the cutting edge (342) from stretching and/or dragging tissue across anvil surface (512) (see FIG. 8) and washer (617) and distally through gap (681), ensuring that tissue is fully severed.

C. Exemplary Anvil Having Breakable Washer with Concentric Annular Ridges

FIG. 16 shows another exemplary washer (717) for use with anvil (500) incorporated into surgical instrument (10). It will be appreciated that washer (717) is similar in structure and function to washer (517) described above except as otherwise described. In particular, and as described in greater detail below, washer (717) of the present example includes a tissue gripping feature in the form of a plurality of concentric annular ridges (782) on a proximal face (780). Proximal face (780) would face toward knife member (340) when a version of anvil (500) incorporating washer (717) is secured to trocar (330).

Each annular ridge (782) has an arcuate shape that extends from proximal face (780). Annular ridges (782) extend proximally at a first angle away from central portion (789) of proximal face (780) and reaches a rounded top portion of annular ridge (782) and turns distally at sharper angle towards a valley of annular ridge (782). Valley of annular ridge (782) is more proximally located than proximal face (580) and has an arcuate shape. A second annular ridge (782) extends proximally at the first angle from valley to top portion. Second annular ridge (782) also turns in a distal direction at a sharper angle than first angle. Sharper angle is aligned with an outer surface (754) of outer wall (750). Annular ridges (782) may be various other suitable shapes such as a pyramid, a cone, a truncate cone, a cylinder, a square, a triangle, a rectangle, a partial sphere, a partial ellipse, or any shape known in the art to provide a gripping surface to grab tissue. Additionally, annular ridges (782) may include barbs (not shown) to further grip and stabilize tissue. Plurality of annular ridges (782) is symmetrically arranged in radially inner and outer rows (792, 794) about proximal face (780). Inner row (722) is spaced a first radial distance from central axis (CA) of washer (717) and arranged along a radially inner portion (788) of proximal face (780). Inner row (792) includes two annular ridges (782) but may include a more or less annular ridges (782).

Outer row (794) is spaced a second radial distance that is greater than first radial distance from central axis (CA) of washer (717) and arranged along a radially outer portion (786) of proximal face (780). Outer row (794) like inner row (722) includes two annular ridges (782) but may include more or less annular ridges (782). The number of annular ridges (782) in outer row (794) may be different than the number of concentric rings in inner row (722), or number of rings may be same. Proximal face (780) further includes a smooth surface (790) located on a central portion (789) between outer and inner portions (586, 588). Smooth surface (790) is configured to allow cutting edge (342) of knife member (340) to evenly engage tissue as knife member (340) is translated distally.

FIG. 17A schematically shows stapling head assembly (300) coupled with anvil (500) with portions omitted for clarity. Knife member (340) is located in a proximal position relative to washer (717) with cutting edge (342) concentrically aligned with central portion (789). In the proximal position, deck member (322) and proximal stapling surface (512) have compressed tissue therebetween providing some distal pressure upon the tissue (see FIG. 7C). In response to this pressure, plurality of annular ridges (782) lightly engages tissue to stabilize tissue on proximal face (780) before knife member (340) is translated distally.

Knife member (340) is translated distally until cutting edge (342) engages tissue providing distal pressure upon the tissue between cutting edge (342) and central portion (789). Tissue conforms around plurality of annular ridges (782), which further engages and stabilizes tissue from stretching or moving. Washer (717) acts as a cutting board while cutting edge (342) cuts through tissue in an abrupt guillotine-type cutting action severing tissue around the circumference of cutting edge (342).

FIG. 17B schematically shows the stapling head assembly (300) and anvil (500) of FIG. 17A. Knife member (340) has translated distally from the proximal position to a distal position and has transected the central portion (789) creating a gap (781) in central portion (789). Washer (717) breaks producing audible and/or tactile feedback to the user to indicate completion of tissue cutting and stapling. As knife member (340) continues to translate distally beyond the proximal wall of washer (717) between inner and outer walls (760, 750), plurality of annular ridges (782) continues to engage and stabilize tissue in a radial direction of washer (717), which inhibits the cutting edge (342) from stretching and/or dragging tissue across anvil surface (512) (see FIG. 8) and washer (717) and distally through gap (781), ensuring that tissue is fully severed.

III. EXEMPLARY WASHERS WITH NORMAL FORCE ENHANCING FEATURES

As noted above, washer (417) is broken by knife member (340) when knife member (340) completes a full distal range of motion from the position shown in FIG. 7C to the position shown in FIG. 7D. In some procedures, it may be desirable to increase the normal force exerted by the opposed broken edges of washer (417) on the sides of knife member (340) as knife member (340) continues to penetrate distally between the broken edges after the initial fracture of the washer (417), for example by providing the proximal wall of washer (417) with an increased thickness to thereby increase a structural rigidity of washer (417). This increase in normal force yields an increase in the resulting friction force exerted by washer (417) on the tissue, thus stabilizing the tissue more effectively and further promoting full cutting of the tissue by knife member (340) as knife member (340) advances distally against washer (417). Exemplary versions of features that may provide the functional benefits noted above, and/or other benefits, via increased structural rigidity of the proximal wall of a washer are described in greater detail below.

A. Exemplary Washer with Arched Proximal Wall

Figure 18:
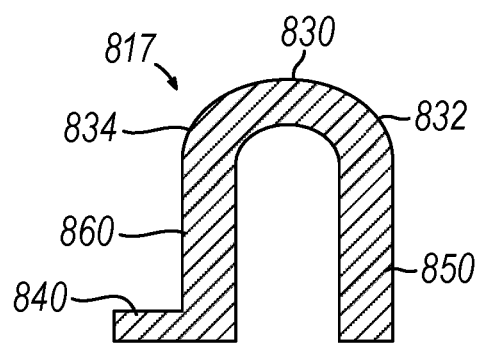
FIG. 18 depicts a partial cross-sectional side view of yet another exemplary washer for use with the anvil of FIG. 8, where the cross-sectional shape of the washer has an arched central portion.

FIG. 18 schematically shows another exemplary washer (817) configured for use with anvil (500) of surgical instrument (10) in place of washer (517). It will be appreciated that washer (817) is similar in structure and function to washer (517) described above except as otherwise described. In particular, washer (517) is suitably configured to exhibit increased structural rigidity relative to washers (417, 517) and thereby exert an increased normal force between the broken edges of washer (817) and the knife (340) during a cutting sequence.

Washer (817) is similar to washer (517) in that washer (817) includes an annular shape extending distally along a central axis from a proximal wall (830) to a distal wall (840). Proximal wall (830) is transversely positioned relative to the central axis. Proximal wall (830) would face toward knife member (340) when a version of anvil (500) incorporating washer (817) is secured to trocar (330). Proximal wall (830) is fixedly secured to a proximal portion of an outer wall (850) at an outer edge (832) of proximal wall (830) and fixedly secured to a proximal portion of an inner wall (860) at an inner edge (834) of proximal wall (830). Washer (817) differs from washer (517) in that proximal wall (830) of washer (817) is arched and may have a greater thickness than the proximal wall of washer (517), thereby providing washer (817) with increase structural rigidity for exerting an increased normal force between the knife (340) and the broken edges of washer (817). In some versions, washer (817) may also include a tissue gripping feature (not shown) similar to tissue gripping feature (582).

B. Exemplary Washer with Peaked Proximal Wall

Figure 19:
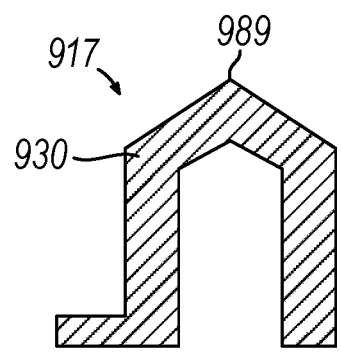
FIG. 19 depicts a partial cross-sectional side view of yet another exemplary washer for use with the anvil of FIG. 8, where the cross-sectional shape of the washer has a peaked central portion.

FIG. 19 schematically shows yet another exemplary washer (917) similar to washer (817) except as otherwise described. Washer (917) is similar to washer (817) in that washer (917) is suitably configured to exhibit increased structural rigidity relative to washers (417, 517) and thereby exert an increased normal force between the broken edges of washer (917) and the knife member (340) during a cutting sequence.

Washer (917) includes a peaked proximal wall (930) configured to confront the knife member (340) at a central portion (989) that defines an annular distal edge. Peaked proximal wall (930) tapers in a proximal direction to central portion (989), thus defining an opposed pair of angular faces that face proximally. Peaked proximal wall (9300 may have a greater thickness than the proximal wall of washer (517). In some versions, washer (917) may also include a gripping feature (not shown) similar to gripping feature (582). In yet other versions, the peaked proximal wall (930) may include a rounded or chamfered face (not shown) in the central portion (989) to facilitate engagement of knife member (340) with washer (917) to prevent transverse deflection of peaked proximal wall (930) or cutting edge (342) of knife member (340) relative to one another.

C. Exemplary Washer with Dual-Tapered Proximal Wall

Figure 20:
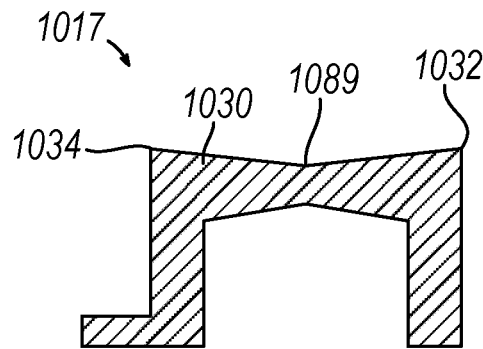
FIG. 20 depicts a partial cross-sectional side view of yet another exemplary washer for use with the anvil of FIG. 8, where the cross-sectional shape of the washer has a tapered central portion.

FIG. 20 schematically shows yet another exemplary washer (1017) similar to washer (817) except as otherwise described. Washer (1017) is similar to washer (817) in that washer (1017) is suitably configured to exhibit increased structural rigidity relative to washers (417, 517) and thereby exert an increased normal force between the broken edges of washer (1017) and the knife member (340) during a cutting sequence.

Washer (1017) includes a dual-tapered proximal wall (1030) having a first larger thickness at each of an outer edge (1032) and an inner edge (1034), and a second smaller thickness at a central portion (1089), which define an average thickness that is greater than the thickness of the proximal wall of washer (517). More specifically, proximal wall (1030) tapers in thickness in a radial direction from each of outer edge (1032) and inner edge (1034) in a direction toward a circumferential centerline of central portion (1089). Proximal wall (1030) would face toward knife member (340) when a version of anvil (500) incorporating washer (1017) is secured to trocar (330). Proximal wall (1030) may include a taper on the proximal side of the proximal wall (1030) and/or the distal side of the proximal wall (1030). This smaller thickness in the central portion (1089) and larger thickness in the inner and outer edges (1034, 1032) allows for increased rigidity of proximal wall (1030) and thus an increase in the normal force while allowing the central portion (1089) to easily cut/break with the knife member (340). In some versions, washer (1017) may also include a tissue gripping feature (not shown) similar to tissue gripping feature (582).

D. Exemplary Washer with Grooved Proximal Wall

Figure 21:
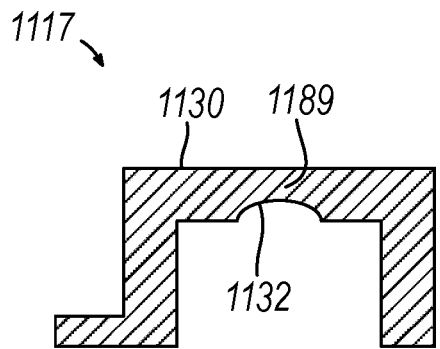
FIG. 21 depicts a partial cross-sectional side view of yet another exemplary washer for use with the anvil of FIG. 8, where the cross-sectional shape of the washer has a grooved central portion.

FIG. 21 schematically shows yet another exemplary washer (1117) similar to washer (1017) except as otherwise described. Washer (1117) is similar to washer (1017) in that washer (1117) is suitably configured to exhibit increased structural rigidity relative to washers (417, 517) and thereby exert an increased normal force between the broken edges of washer (1117) and knife member (340) during a cutting.

Washer (1117) includes a proximal wall (1130) having a first larger thickness at each of a radially outer edge and a radially inner edge that is greater than a thickness of the proximal wall of washer (417), and a second smaller thickness at a central portion (1189). In the present example, this smaller thickness of central portion (1189) is defined by an annular groove (1132) on the distal side of proximal wall (1130). In other versions, though not shown, annular groove (1132) may be provided on the proximal side of proximal wall (1130) in place of or in addition to being provided on the proximal side. The enlarged thickness at the radially inner and outer edges allows for increased rigidity of proximal wall (1130) and thus increased normal force, while the lesser thickness of central portion (1189) enables proximal wall (1130) to be easily cut by knife member (340). In some versions, washer (1117) may also include a tissue gripping feature (not shown) similar to tissue gripping feature (582).

E. Exemplary Washer with Multi-Layer Wall

Figure 22:
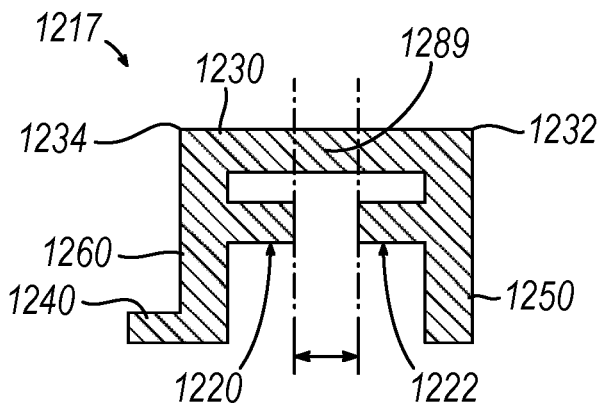
FIG. 22 depicts a partial cross-sectional side view of yet another exemplary washer for use with the anvil of FIG. 8, where the washer has a multi-layered construction.

FIG. 22 schematically shows yet another exemplary washer (1217) that is similar to washer (517) except as otherwise described, and that is suitably configured to exhibit increased structural rigidity relative to washers (417, 517) and thereby exert an increased normal force between the broken edges of washer (1217) and knife member (340) during a cutting sequence. A proximal wall (1230) of washer (1217) is fixedly secured to a proximal portion of an outer wall (1250) at an outer edge (1232) of proximal wall (1230) and fixedly secured to a proximal portion of an inner wall (1260) at an inner edge (1234) of proximal wall (1230). Proximal wall (1230) would face toward knife member (340) when a version of anvil (500) incorporating washer (1217) is secured to trocar (330).

Washer (1217) further includes first and second annular projections (1220, 1222). First annular projection (1220) is fixedly secured to an inner portion of inner wall (1260) and extends radially outwardly from the inner wall (1260) towards outer wall (1250) parallel to the proximal wall (1230). First annular projection (1220) terminates radially before central portion (1289). Second annular projection (1222) extends radially inwardly from the outer wall (1250) towards inner wall (1260). Second annular projection (1222) is fixedly secured to an inner portion of outer wall (1250), extends parallel to the proximal wall (1230), and terminates radially before the central portion (1289). Accordingly, first and second annular projections (1220, 1222) have free edges that confront and are spaced apart from one another in a radial direction, thus defining an annular gap between their confronting free edges. In some versions, though not shown, first and second annular projections (1120, 1122) extend into the central portion (1289) and are fixedly secured together. In some versions, proximal wall (1230) may be shaped alternatively similar to washers (817, 917, 1017, 1117). In yet other versions, washer (1217) may also include a tissue gripping feature (not shown) similar to tissue gripping feature (582).

F. Exemplary Washers with Dual Density Proximal Wall

Figure 23:
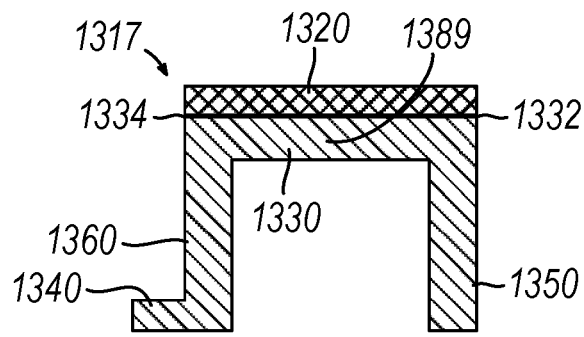
FIG. 23 depicts a partial cross-sectional side view of yet another exemplary washer for use with the anvil of FIG. 8, where a proximal side of the washer includes a coating.

FIG. 23 schematically shows yet another exemplary washer (1317) that is similar to washer (517) except as otherwise described, and that is suitably configured to exhibit increased structural rigidity relative to washers (417, 517) and thereby exert an increased normal force between the broken edges of washer (1317) and knife member (340) during a cutting sequence. Washer (1317) includes an annular shape extending distally along a central axis from a proximal wall (1330) to a distal wall (1340). Proximal wall (1330) is transversely positioned relative to the central axis. Proximal wall (1330) would face toward knife member (340) when a version of anvil (500) incorporating washer (1317) is secured to trocar (330). Proximal wall (1330) is fixedly secured to a proximal portion of an outer wall (1350) at an outer edge (1332) of proximal wall (1330) and fixedly secured to a proximal portion of an inner wall (1360) at an inner edge (1334) of proximal wall (1330).

Washer (1317) differs from washer (517) in that washer (1317) includes a multi-layer proximal wall (1330) constructed of more than one material arranged in distinct layers. Proximal wall (1330) further includes a coating (1320) that extends radially from inner edge (1334) to outer edge (1332) on a proximal side of proximal wall (1330). In the present version, coating (1320) includes a soft polymer that increases a rigidity of washer (1317) and thus the normal force between the washer (1317) and the knife member (340) while allowing the central portion (1389) to easily cut/break with the knife member (340). In some versions, the proximal wall (1330) may include other features similar to washers (817, 917, 1017, 1117). In yet other versions, washer (1317) may also include a tissue gripping feature (not shown) similar to tissue gripping feature (582).

Figure 24:
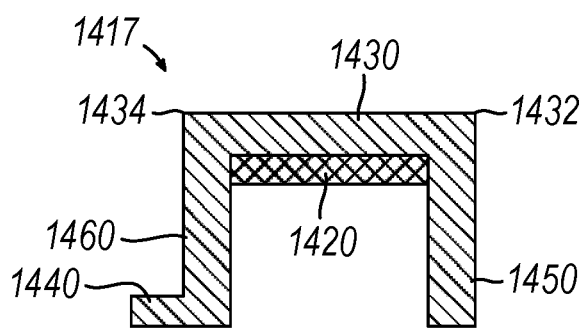
FIG. 24 depicts a partial cross-sectional side view of yet another exemplary washer for use with the anvil of FIG. 8, where a distal side of the washer includes a coating.

FIG. 24 schematically shows yet another exemplary washer (1417) that is similar to washer (517) except as otherwise described, and that is suitably configured to exhibit increased structural rigidity relative to washers (417, 517) and thereby exert an increased normal force between the broken edges of washer (1417) and knife member (340) during a cutting sequence. Washer (1417) is similar to washer (1317) but differs in that a coating (1420) is on the distal side of proximal wall (1430), rather than the proximal side of the proximal wall (1330) as in washer (1317). Coating (1420) extends radially from an inner wall (1460) to an outer wall (1450). Coating (1420) is similar in structure and function to coating (1320) of washer (1317). In some versions, the proximal wall (1430) may include other features similar to washers (817, 917, 1017, 1117). In yet other versions, washer (1417) may also include a tissue gripping feature (not shown) similar to tissue gripping feature (582).

IV. EXEMPLARY END EFFECTORS HAVING AUXILIARY TISSUE COMPRESSION MEMBERS

In some instances, it may be desirable to include an auxiliary tissue compression member within the stapling head assembly (300) that aids in clamping the tissue along the radially inner side of knife member (340), apart from the stapling surfaces of end effector (300), to more effectively stabilize the tissue in a radial direction and thereby enable knife member (340) to fully cut the tissue. Exemplary versions of such features are described in greater detail below. It will be appreciated that any of the exemplary auxiliary tissue compression members described below may be combined with any of the exemplary washers described above.

A. End Effector Having a Resiliently Compressible Tissue Compression Member

Figure 25:
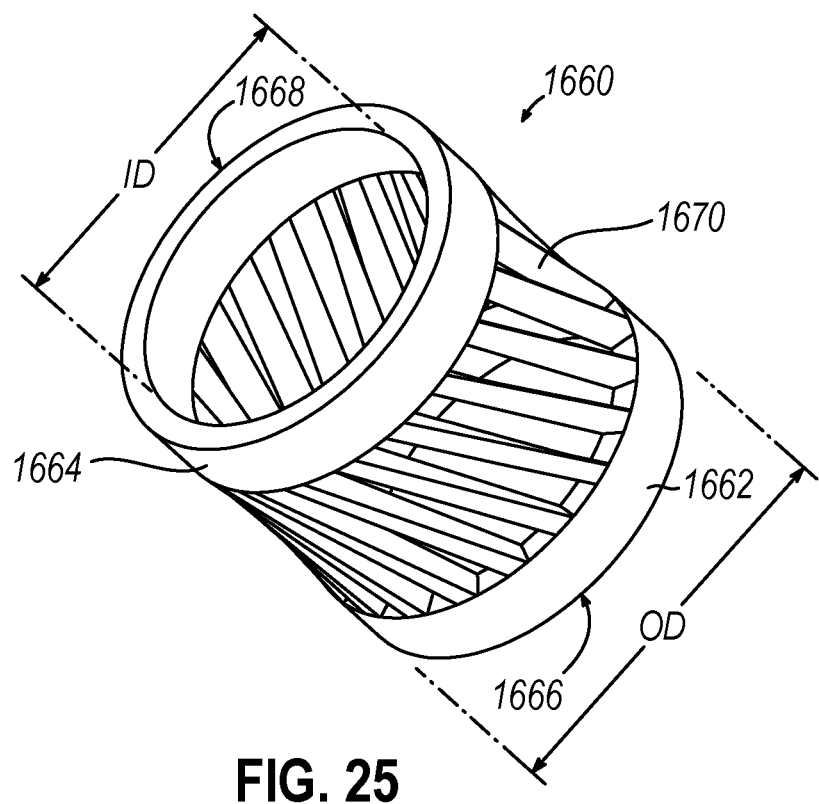
FIG. 25 depicts a perspective view of an exemplary compressible auxiliary tissue compression member for use with an end effector of a circular surgical stapler.
Figure 26A:
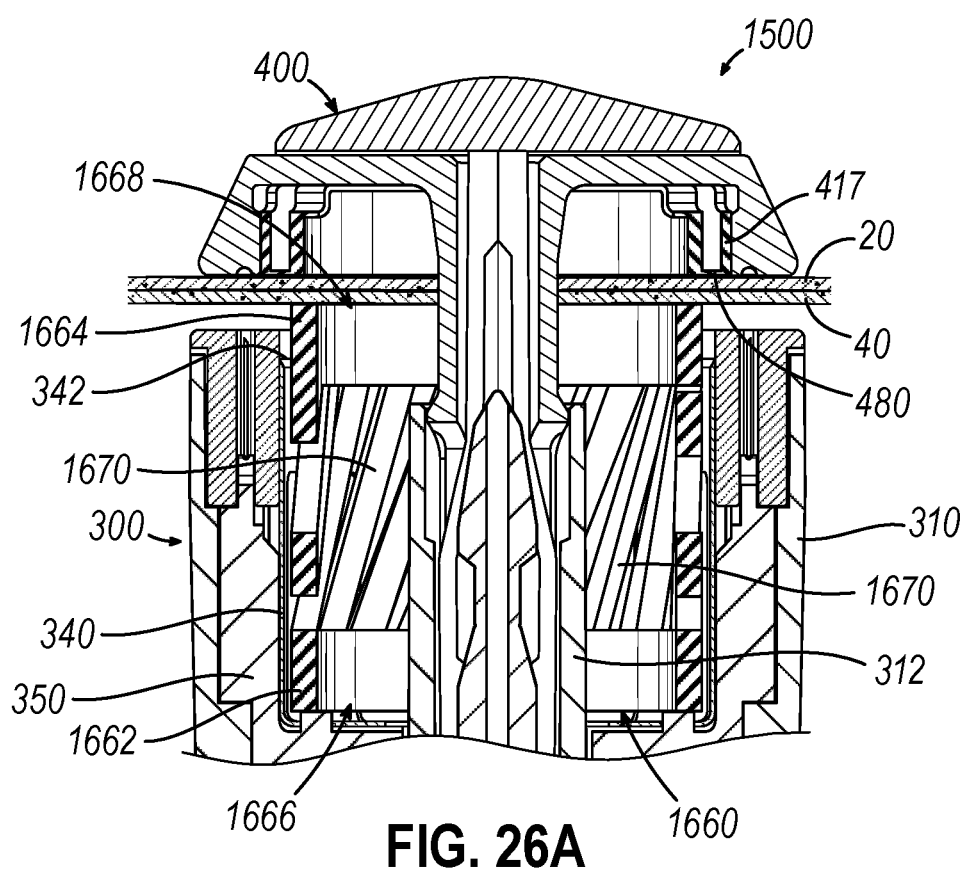
FIG. 26A depicts a cross-sectional view of an exemplary end effector including the anvil of FIG. 3 and the stapling head assembly of FIG. 4 having the auxiliary tissue compression member of FIG. 25, with the end effector in an open state such that its anvil surface is spaced apart from its deck surface, and with the auxiliary tissue compression member in an axially non-compressed state.
Figure 26B:
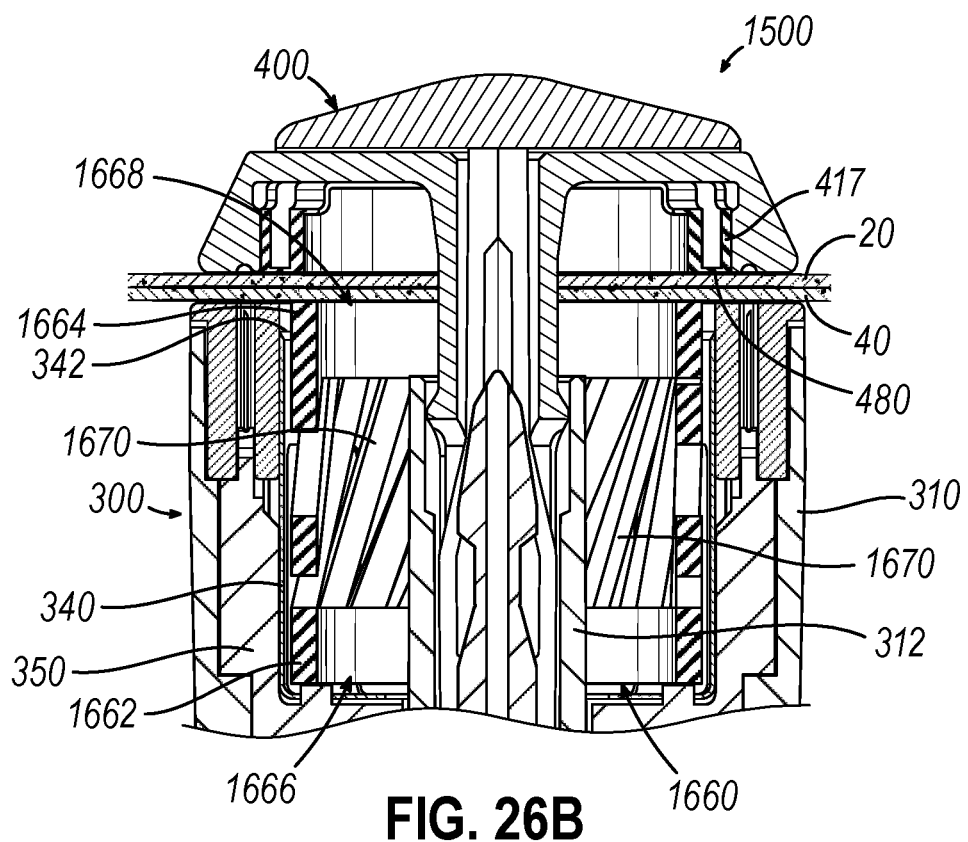
FIG. 26B depicts another cross-sectional view of the end effector of FIG. 26A, with the anvil proximally retracted towards the stapling head assembly to clamp tissue in a closed state of the end effector, and with the auxiliary tissue compression member in a first axially compressed state in which it exerts a distal compression force on tissue and the anvil washer.
Figure 26C:
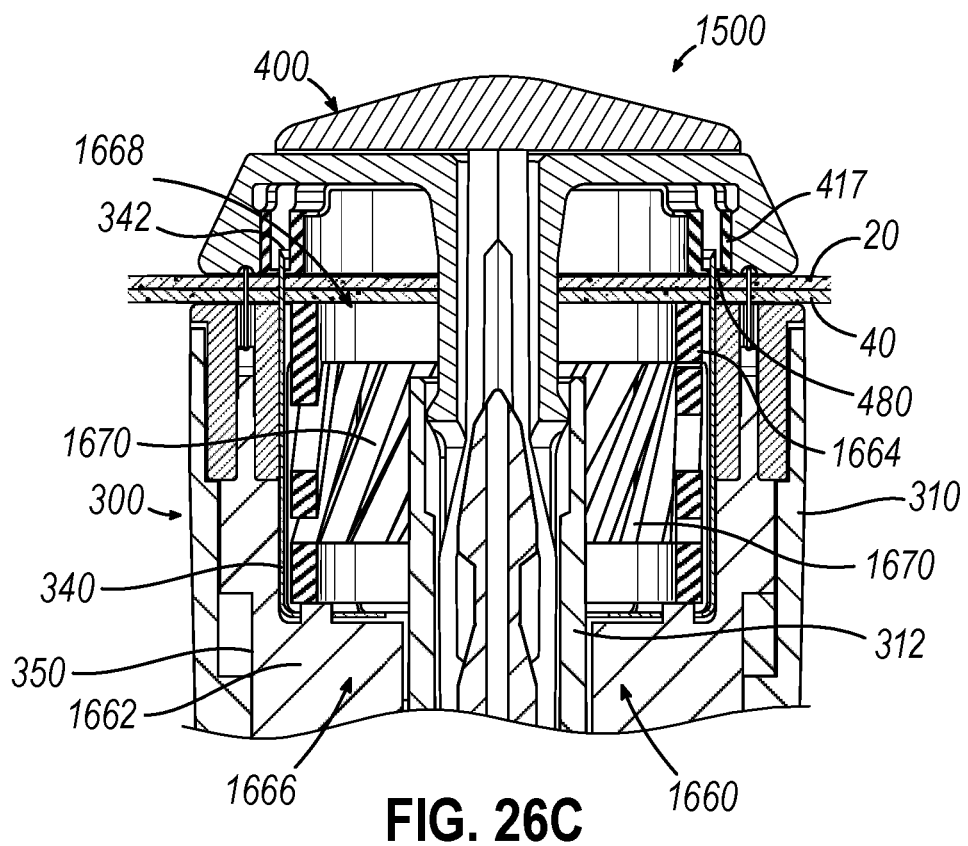
FIG. 26C depicts another cross-sectional view of the end effector of FIG. 26A, with the knife member advanced distally to cut tissue and with the auxiliary tissue compression member in a second axially compressed state in which it exerts a distal compression force on tissue and the anvil washer.

FIGS. 25-26C show an end effector (1500) including anvil (400) and stapling head assembly (300), which includes an auxiliary tissue compression member in the form of a resiliently compressible member (1660) positioned radially inwardly of and adjacent to knife member (340).

As shown in FIG. 25, resiliently compressible member (1660) includes a proximal ring (1662) having a proximal face (1666), a distal ring (1664) having a distal face (1668), and a plurality of resilient splines (1670) collectively defining a lattice that interconnects proximal and distal rings (1662, 1664). Resilient splines (1670) give compression member (1660) resilient properties that allow the resiliently compressible member (1660) to be axially-compressed. Resiliently compressible member (1660) has a cylindrical shape that defines an outer diameter (OD) that is just smaller than a diameter defined by an inner diameter of knife member (340). Compression member also defines an inner diameter (ID) configured to receive core member (312) of body member (310) within the inner diameter (ID). Proximal face (1666) of proximal ring (1662) is configured to be anchored to a proximal hub of knife member (340) or a proximal portion of the staple driver member (350) such that only the distal end of resiliently compressible member (1660) is moveable relative to the knife member (340) when the resiliently compressible member (1660) is compressed. It should be noted, resiliently compressible member (1660) may be installed within stapling head assembly (300) without any modification or structural changes to stapling head assembly (300). Distal ring (1664) of resiliently compressible member (1660) aligns with a proximal face of washer (417) such that distal face (1668) of distal ring (1664) is configured to clamp tissue against a radially inner portion of proximal face of washer (417), thereby stabilizing the tissue radially, when end effector (1500) is closed and fired on tissue, as described below.

FIG. 26A shows the anvil (400) spaced apart from the deck surface (322), resiliently compressible member (1660) and tissue. End effector (1500) is shown prior to tissue clamping with resiliently compressible member (1660) in a neutral, axially expanded state in which the distal face (1668) of the resiliently compressible member (1660) extends distally beyond the deck surface (522) and is distal of the knife edge (342). Distal face (1668) is configured to engage tissue before the knife edge (342) and engage tissue when the anvil (400) is retracted proximally.

FIG. 26B shows the anvil (400) retracted proximally toward stapling head assembly (300) to clamp the tissue against the deck surface (322). In response to this proximal retraction of anvil (400), resiliently compressible member (1660) compresses proximally to a first axially compressed state in which distal face (1668) is approximately flush with deck surface (322) and is compressing tissue distally against proximal face (480) of washer (417). In this first compressed state, distal face (1668) exerts a distal spring compression force on tissue that overlies the proximal face of washer (417), thereby constraining the tissue in a radial direction at a location radially inwardly of and adjacent to knife member (340), along the inner diameter of knife member (340).

FIG. 26C shows the knife member (340) having been advanced distally to cut the tissue while the tissue remains clamped between distal face (1668) of resiliently compressible member (1660) and proximal face (480) of washer (417), with resiliently compressible member (1660) being further compressed axially to a second, fully axially compressed state. Further axial compression of resiliently compressible member (1660) may increase the distally directed spring force exerted on the tissue along inner diameter of knife member (340) and thereby more securely clamp that region of tissue against washer (417) as knife edge (342) passes distally through the tissue and washer (417), thus enabling knife member (340) to fully cut the tissue.

B. End Effector Having a Translatable Tissue Compression Member

Figure 27:
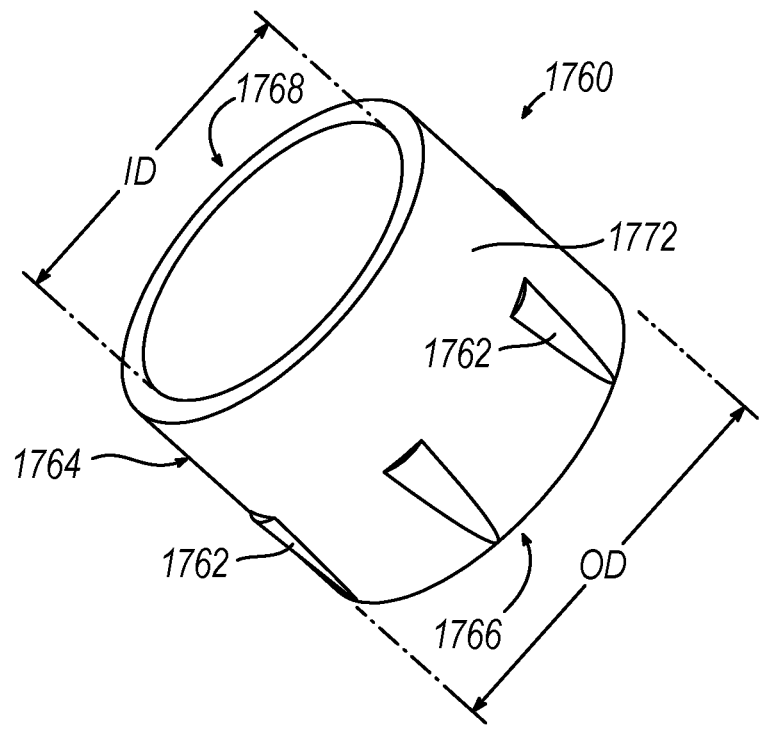
FIG. 27 depicts a perspective view of an exemplary translatable auxiliary tissue compression member for use with an end effector of a circular surgical stapler.

FIG. 27 shows another exemplary auxiliary tissue compression member in the form of a translatable member (1760) that may be installed radially inwardly of and adjacent to knife member (340) of stapling head assembly (300). Translatable member (1760) includes a cylindrical body (1764) that extends longitudinally from a proximal face (1766) to a distal face (1768), and a plurality of interfering bumps (1762) positioned circumferentially, symmetrically about an outer surface (1772) of body (1764). Translatable member (1760) of the present version has a maximum outer diameter (OD) defined by interfering bumps (1762) that is just larger than an inner diameter of knife member (340). Accordingly, interfering bumps (1762) are configured to directly contact and slightly deform against the radially inner surface of knife member (340), thus providing an interference fit between translatable member (1760) and knife member (340) with a suitable degree of frictional force that enables translatable member (1760) to releasably maintain a longitudinal position relative to knife member (340) while still being slidable relative to knife member (340) in response to an external force. In some other versions, the outer surface (1772) additionally engages the inner diameter of the knife member (340). Translatable member (1760) also defines an inner diameter (ID) configured to receive core member (312) of body member (310) within the inner diameter (ID). Translatable member (1760) may be constructed of a resilient material such as foam, rubber, or plastic. Body (1764) has resilient properties that allows body (1764) to radially expand within inner diameter of knife member (340) to retain body (1764) within the knife member (340). Interfering bumps (1762) are configured to provide additional friction within inner diameter of knife member (340). Interfering bumps (1762) include a tapered surface extending in an axial direction that have a larger distal portion than a relatively smaller proximal portion.

Similar to resiliently compressible member (1660) described above, distal face (1768) of translatable member (1760) aligns with proximal face (480) of washer (417) such that distal face (1768) is configured to clamp tissue against a radially inner portion of proximal face (480), thereby stabilizing the tissue radially when end effector (1500) is closed and fired on tissue, as described below.

Figure 28A:
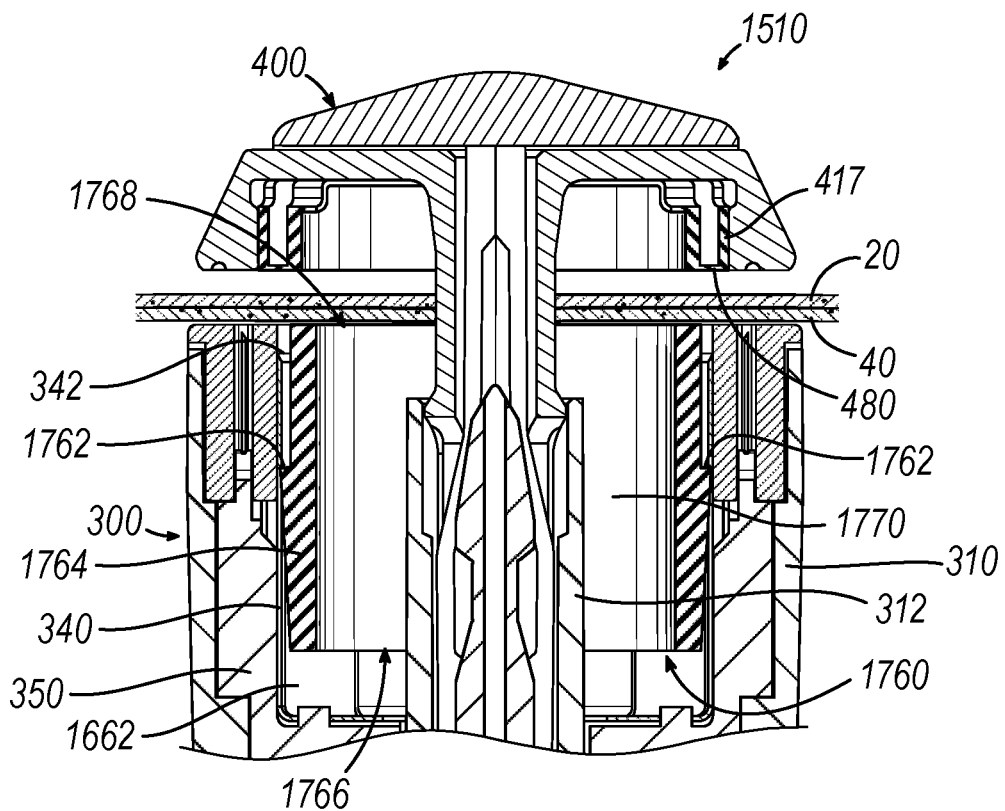
FIG. 28A depicts a cross-sectional view of an exemplary end effector including the anvil of FIG. 3 and the stapling head assembly of FIG. 4 having the auxiliary tissue compression member of FIG. 27, with the end effector in an open state such that its anvil surface is spaced apart from its deck surface, and with the auxiliary tissue compression member distally located in a first position relative to the cutting edge of the knife member.

FIG. 28A shows anvil (400) spaced distally from the stapling head assembly (300) and the tissue prior to clamping tissue. Translatable member (1760) is positioned with distal face (1768) distally located relative to deck surface (322) and the knife edge (342). Proximal face (1766) is spaced apart from hub and a proximal portion of the staple driver member (350). Interfering bumps (1762) are longitudinally retaining the translating member (1760) within inner diameter of knife member (340) in a distal position. Distal face (1768) is configured to engage tissue before the knife edge (342) when the anvil (400) is retracted proximally.

Figure 28B:
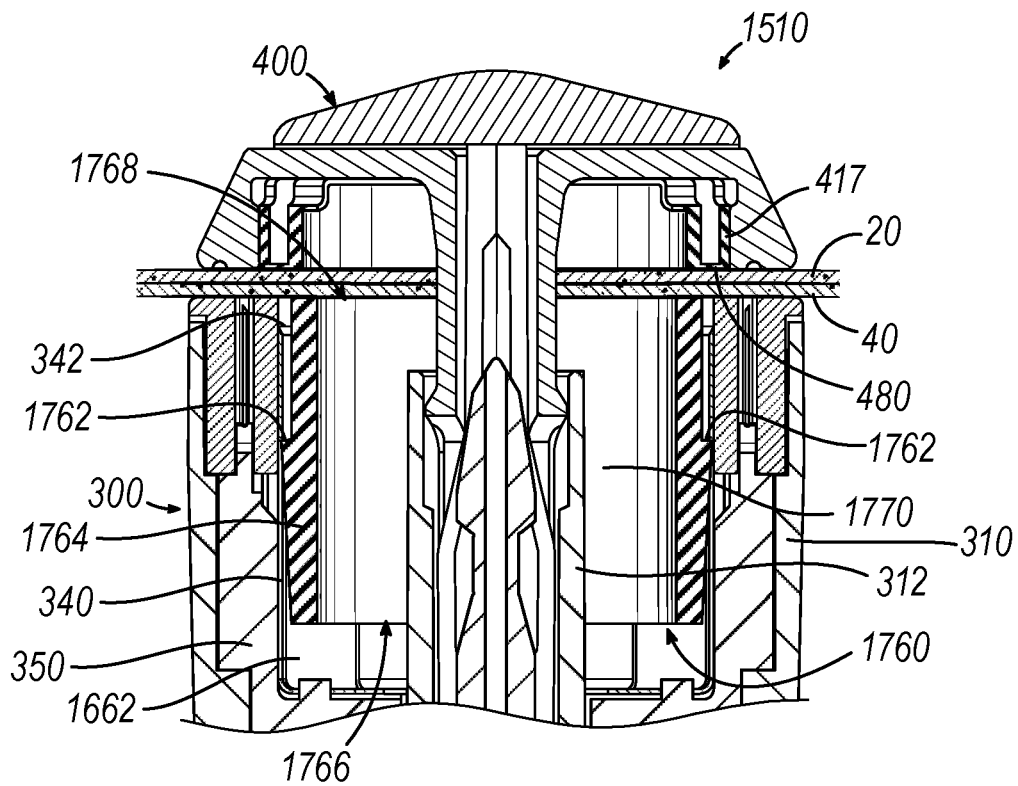
FIG. 28B depicts another cross-sectional view of the end effector of FIG. 28A, with the anvil retracted proximally towards the stapling head assembly to clamp tissue in a closed state of the end effector, and with the translatable member distally located in the first position relative to the cutting edge of the knife member.

FIG. 28B shows anvil (400) being retracted proximally to clamp tissue against deck surface (322) and distal face (1768) of translating member (1760). As anvil (400) is retracted proximally to clamp tissue against stapling head assembly (300), proximal face of anvil washer (417) contacts the tissue at a location radially inwardly of knife member (340) and exerts a proximal force through the tissue and against distal face (1768) of translatable member (1760), thereby anchoring translatable member (1760) in a distal direction relative to tissue and washer (417). The proximally directed force imparted on translatable member (1760) by washer (417), through the clamped tissue, overcomes the friction force exerted between the deformed interfering bumps (1762) of translatable member (1760) and radially inner surface of knife member (340), thus causing translatable member (1760) to translate proximally relative to knife member (340) as anvil (400) retracts proximally toward stapling head assembly (300). When anvil (400) reaches a suitable proximal position relative to stapling head assembly (300), translatable member (1760) maintains its longitudinal position relative to knife member (340) via the friction force between the deformed interfering bumps (1762) and knife member (340). Accordingly, in the closed position of anvil (400), distal face (1768) of translatable member (1760) exerts a distally directed force compressing the tissue against the proximal face of washer (417), thereby constraining the tissue radially at a location radially inwardly of knife member (340).

Figure 28C:
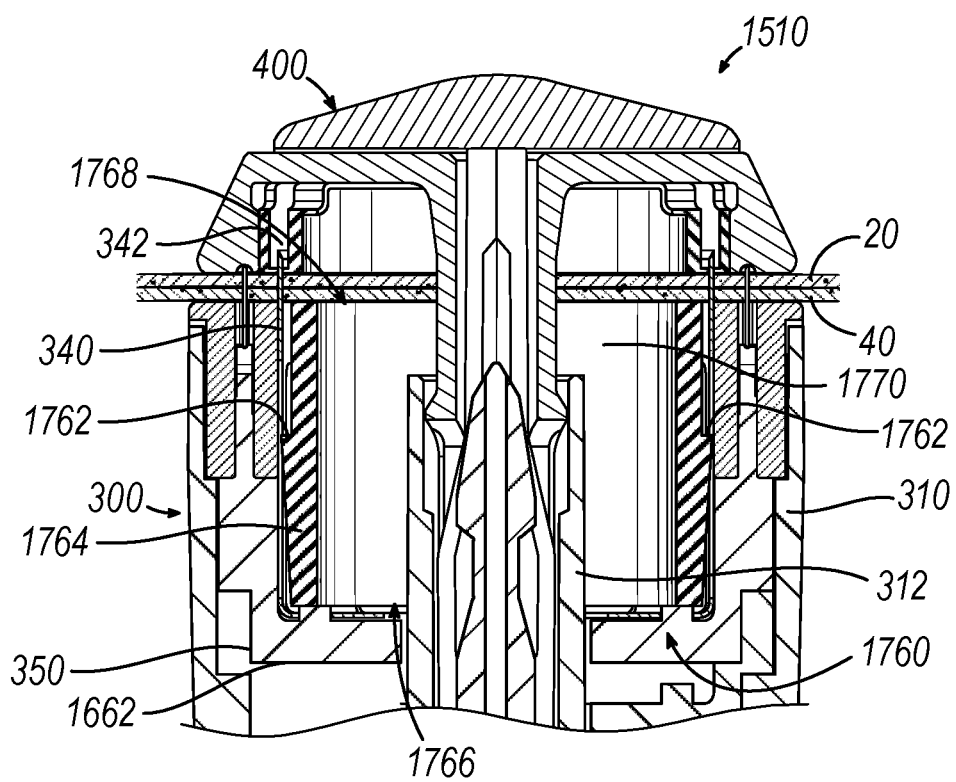
FIG. 28C depicts another cross-sectional view of the end effector of FIG. 28A, with the knife member advanced distally to cut tissue and with auxiliary tissue compression member translated proximally so that translatable member is proximally located relative in a second position to the cutting edge of the knife member.

FIG. 28C shows knife member (340) having been advanced distally during a firing stroke of stapler (10) to cut the tissue while tissue remains clamped between distal face (1768) of translating member (1760) and the proximal face (480) of washer (417). Because distal face (1768) of translatable member (1760) is anchored distally against tissue and proximal face (480) of washer (417), as described above, knife member (340) advances distally relative to translatable member (1760) during the firing stroke. This positions translatable member (1760) in a proximal-most position relative to knife member (340) in which proximal face (1766) of translatable member (1760) may be spaced apart from or directly contact a proximal hub of knife member (340), which in turn is affixed to an inner base surface of staple driver member (350). In either case, when translatable member (1760) is in its proximal-most position relative to knife member (340), distal face (1768) continues to compress the tissue distally against proximal face (480) of washer (417), thereby constraining the tissue in a radial direction as knife member (340) cuts distally through the tissue and proximal face (480) of washer (417).

In some versions, proximal face (1766) of translatable member (1760) does not engage proximal hub of knife member (340) or any portion of the staple driver member (350) when stapler (10) is fully fired, such that the distal compression force exerted by translatable member (1760) against tissue and washer (417) is a product of the friction between the interfering bumps (1762) and/or outer surface of body (1764) acting upon the inner diameter of the knife member (340). It should be noted that the friction force created by the interference fit of the interfering bumps (1762) does not significantly increase the force to fire. In other versions, translatable member (1760) in its proximal-most position relative to knife member (340) may engage proximal hub or a proximal portion of the staple driver member (350) and slightly compress proximally to provide additional spring force exerted by the translatable member (1760) against the tissue and washer (417). In yet other versions, though not shown, the radially inner surface of knife member (340) may include pockets configured to retain interfering bumps (1762) so that translatable member (1760) may be installed to a particular longitudinal distance within the inner diameter of the knife member (340) during assembly, and the interfering bumps (1762) may provide frictional resistance when not positioned within the pockets.

In other versions, surgical instrument (10) may be provided with an auxiliary tissue compression member that is positioned radially outwardly of and adjacent to knife member (340) such that a distal end of the auxiliary tissue compression member is configured to directly contact and compress tissue distally at a location radially outwardly of knife member (340), such as against the proximal face of the washer and/or against the anvil stapling surface. For instance, some such versions may employ variations of resiliently compressible member (1660) or translatable member (1760) described above.

V. EXEMPLARY END EFFECTOR WITH ANVIL GAP REDUCTION FEATURES

As noted above, knob (130) (see FIG. 6) adjusts a gap distance (d) between the stapling surface (412) of anvil (400) and the deck surface (322) of stapling head assembly (300) until a minimum gap distance exists between the stapling surface (412) and the deck surface (1822). However, tissue approximately the size of this gap may be difficult to stabilize sufficiently to enable complete cutting of the tissue without uncut portions of tissue being pushed distally between the severed edges of broken washer (417). Accordingly, in some procedures, it may be desirable to provide end effector (300) with one or more rigid features configured to more securely stabilize thin tissue along the inner perimeter of knife member (340) to ensure that the tissue is fully cut. Exemplary versions of such features are described in greater detail below.

A. Deck Member with Raised Annular Rib

Figure 29:
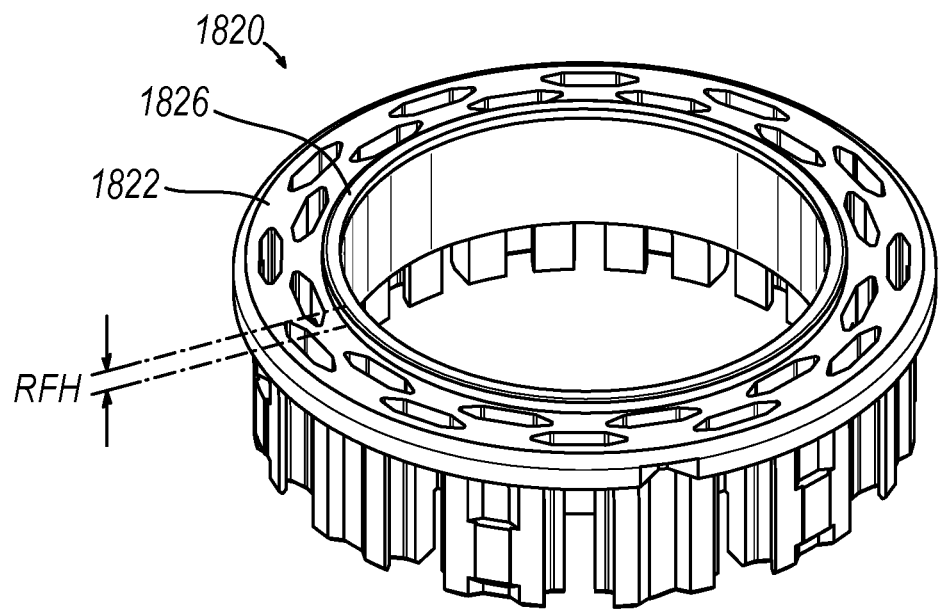
FIG. 29 depicts a perspective view of another exemplary deck member configured for use with the stapling head assembly of FIG. 4, where the deck member includes a raised feature on the deck surface.
Figure 30:
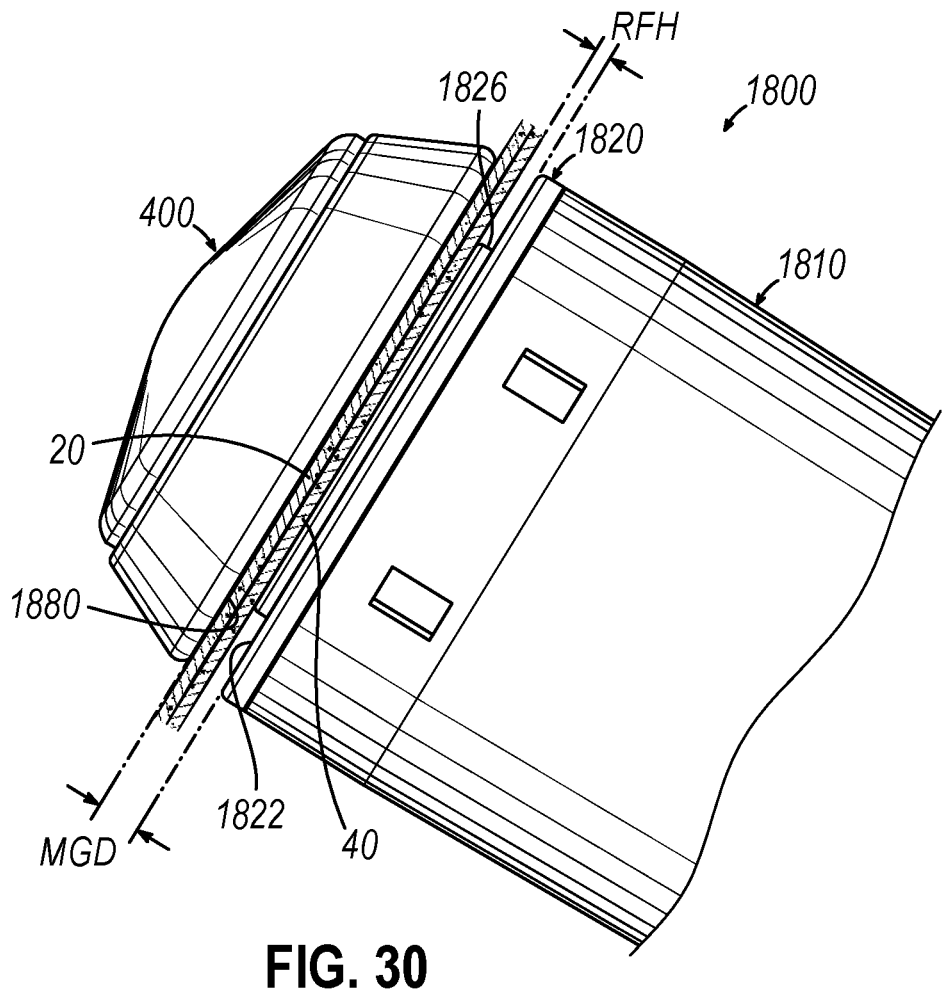
FIG. 30 depicts a perspective side view of a yet another exemplary end effector including the anvil of FIG. 3 and another stapling head assembly with the deck member of FIG. 29, with the end effector in a closed state.

FIGS. 29-30 show a stapling head assembly (1810) having an exemplary alternative deck member (1820). Stapling head assembly (1810) and deck member (1820) are similar in structure and function to stapling head assembly (300) and deck member (320), except as detailed below. Deck member (1820) includes a deck surface (1822) having a raised feature (1826) in the form of an annular rib positioned on a radially inner portion of the deck surface (1822). Raised feature (1826) has an annular shape and extends distally from the radially inner portion of deck surface (1822). Raised feature (1826) of the present example is a rigid feature that may be formed integrally with deck member (1820). As described below, raised feature (1826) is configured to compress tissue distally against washer (417) of anvil (400), and thereby more securely stabilize the tissue radially at a location radially inwardly of knife member (340) to enable complete cutting of the tissue when stapler (10) is fired.

Raised feature (1826) includes a raised feature height (RFH) defined as the distance from a distal end of raised feature (1826) to deck surface (1822). Raised feature height (RFH) is approximately the same distance as a minimum gap distance (MGD) achievable by end effector in a closed state. Thus, the distal end of raised feature (1826) is configured to compress even thin tissue distally against a radially inner portion of proximal face (480) of washer (417) such there is no remaining axial gap between the tissue and either anvil (400) or stapling head assembly (1810), at a location radially inwardly of knife member (340), that might otherwise permit the thin tissue to slide or stretch during a firing sequence of stapler (10). Thin tissue is generally defined as tissue that has a thickness that is slightly smaller than, the same as, or slightly greater than the minimum gap distance (MGD).

B. Washer with Raised Annular Rib

Figure 31:
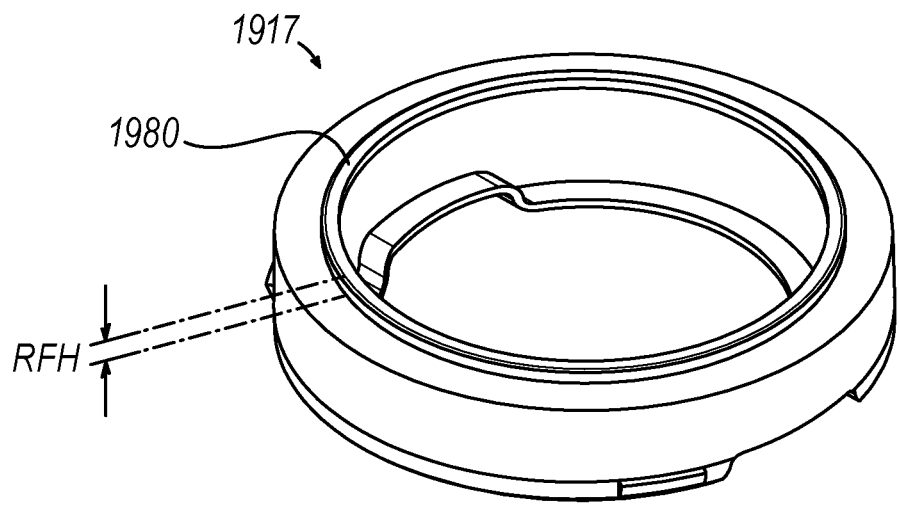
FIG. 31 depicts a perspective view of yet another exemplary washer having a raised feature for use with a surgical stapler end effector.

In some instances, it may be desirable to relocate raised feature (1826) of deck member (1820) described above onto the proximal face of washer (417) of anvil (400) to achieve a similar functional benefit as described above. FIG. 31 shows an exemplary washer (1917) for incorporating into anvil (400) for use with stapling head assembly (300). Washer (1917) is similar in structure and function to washer (417) of anvil (400), except as detailed below. Washer (1917) differs from washer (417) in that washer (1917) includes a raised feature (1926) similar to raised feature (1826). Raised feature (1926) is shown in the form of an annular rib positioned on a radially inner portion of the proximal face (1980).

When washer (1917) is installed in the anvil (400), raised feature (1826) extends proximally from the radially inner portion of proximal face (1980) towards deck surface (1822) to a raised feature height (RFH). Raised feature height (RFH) is the distance from the proximal end of the raised feature (1826) to the proximal face (1980). Raised feature height (RFH) is approximately the same distance as the minimum gap distance (MGD). Thus, the proximal end of raised feature (1826) is configured to compress even thin tissue proximally against a corresponding feature of stapling head assembly (300) such there is no remaining axial gap between the tissue and either anvil (400) or stapling head assembly (300), at a location radially inwardly of knife member (340), that would otherwise permit the thin tissue to slide or stretch during a firing sequence of stapler (10). In other versions, though not shown, a first raised feature may be provided on washer (418) and a second raised feature may be provided on deck surface (322), where the first and second raised features define a combined raised feature height (RFH) that equals the minimum gap distance (MGD).

C. Washer and Deck Member with Nested Tissue Gripping Features

Figure 32:
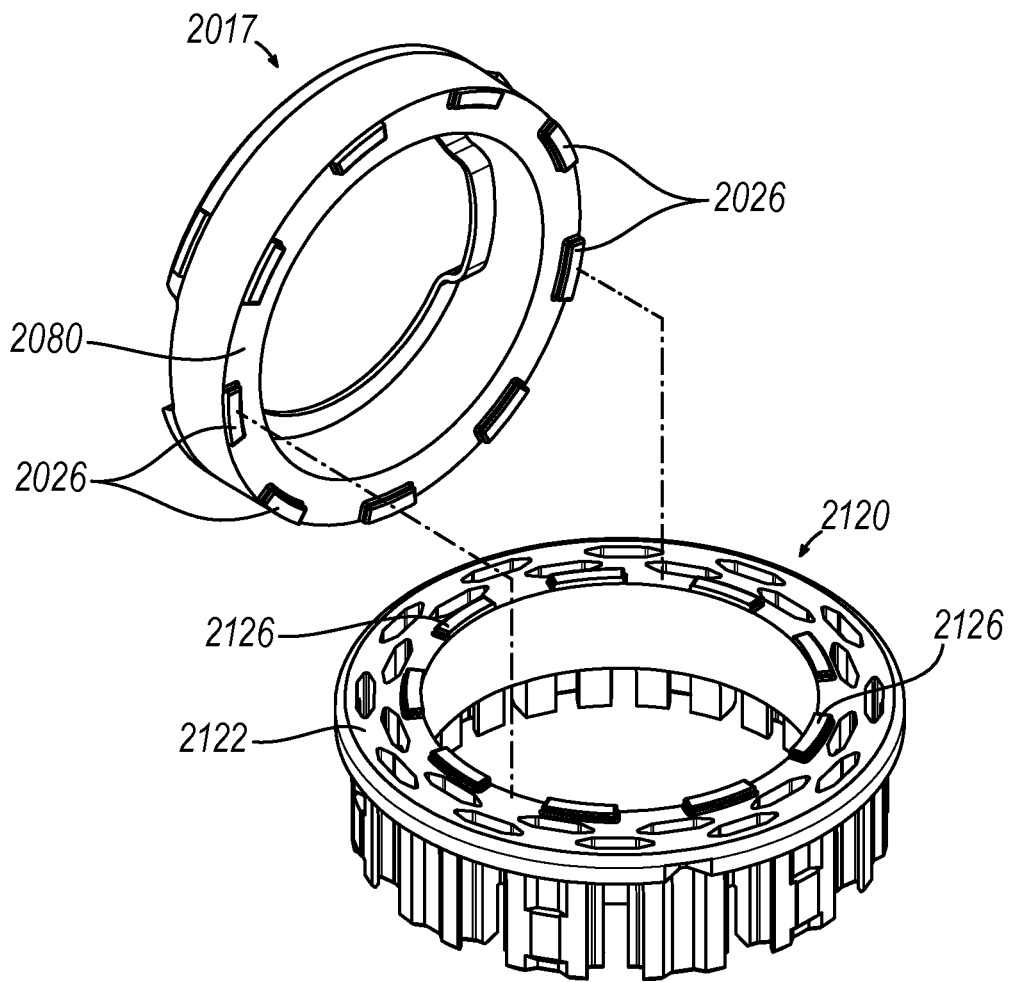
FIG. 32 depicts a composite perspective view of another exemplary washer and another exemplary deck member configured for use with a circular stapler end effector, where each of the washer and the deck member has tissue gripping features.
Figure 33A:
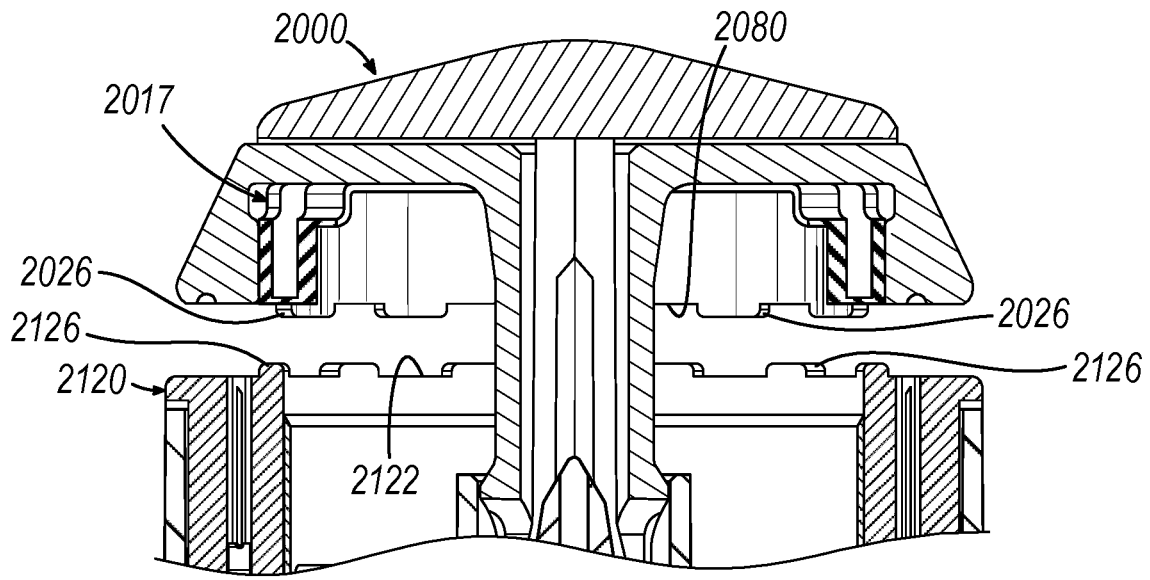
FIG. 33A depicts a cross-sectional view of another exemplary end effector including an anvil having the washer of FIG. 32 and a stapling head assembly having the deck member of FIG. 32, with the anvil spaced apart from the stapling head assembly in an open state of the end effector.
Figure 33B:
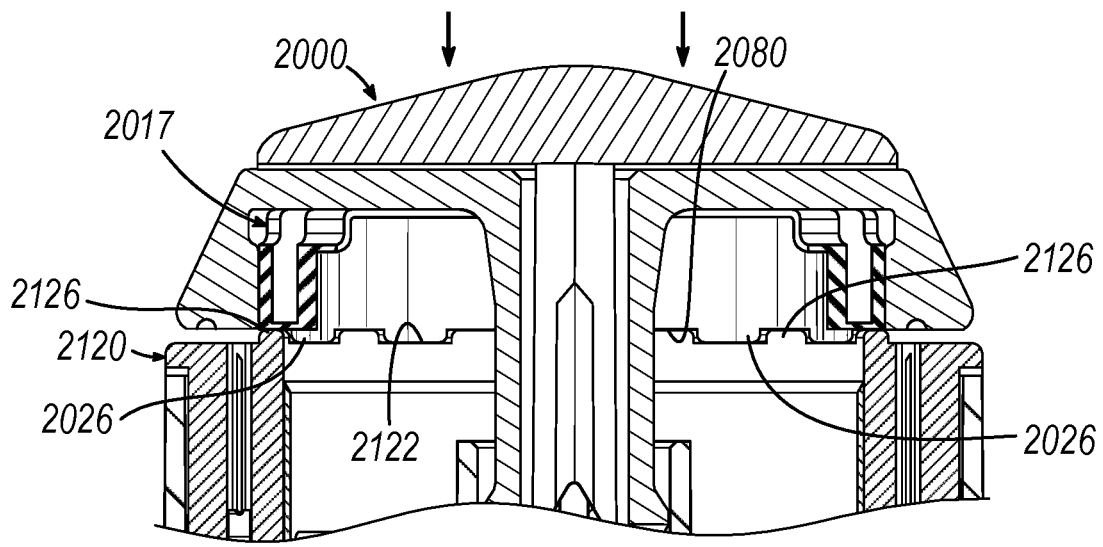
FIG. 33B depicts another cross-sectional view of the end effector of FIG. 33A in a closed state such that the gripping features of the washer nest within the gripping features of the deck surface.

FIGS. 32-33B show an exemplary alternative anvil (2000) and a stapling head assembly (2100) that are similar to anvil (400) and stapling head assembly (300) described above except as otherwise described below. As shown best in FIG. 32, anvil (2000) includes a washer (2017) that includes a first plurality of tissue gripping features (2026) arranged in an annular array on a radially inner portion of the proximal face (2080). Stapling head assembly (2100) includes a deck member (2120) that includes a second plurality of tissue gripping features (2126) arranged in an annular array on radially inner portion of the deck surface (2122). Gripping features (2026) of washer (2017) are configured to be nested within gripping features (2126) of deck member (2120) when anvil (2000) is retracted proximally to clamp tissue against stapling head assembly (2100). Gripping features (2126) extend proximally from the proximal face (2080) towards deck surface (2122), and gripping features (2026) extend distally from the deck surface (2122) towards the proximal face (2080). As described below, tissue gripping features (2026) are configured to nest and thereby cooperate with tissue gripping features (2126) when anvil (2000) is retracted proximally toward stapling head assembly (2100) to more securely grip and stabilize tissue to promote complete cutting of the tissue. By being "nested," tissue gripping features (2026, 2126) are angularly spaced apart from each other such that each tissue gripping feature (2026) will be angularly positioned between two adjacent tissue gripping features (2126), and such each tissue gripping feature (2126) will be angularly positioned between two adjacent tissue gripping features (2026), when anvil (2000) is in a proximally retracted position relative to stapling head assembly (2100).

FIG. 33A shows anvil (2000) spaced distally from deck surface (2122) prior to clamping tissue, such that tissue gripping features (2026) are spaced distally from tissue gripping features (2126).

FIG. 33B shows anvil (2000) after having been approximated toward the stapling head assembly (2100) to a closed position. Gripping features (2026, 2126) are nested within each other and thereby engage both sides of tissue to more securely stabilize the tissue in a radial direction when the tissue is cut by knife member (340). It will be appreciated that each of gripping features (2026) and gripping features (2126) may each be sized, shaped, and spaced apart circumferentially along the respective end effector surface in a variety of manners suitable to effectively grip and thereby stabilize tissue radially and circumferentially during a firing sequence. For instance, gripping features (2026, 2126) may be arranged such that each gripping feature (2026) is circumferentially spaced apart from the circumferentially adjacent gripping features (2126) by a distance suitable to promote effective gripping of tissue while avoiding causing trauma to the tissue.

VI. EXEMPLARY COMBINATIONS

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a stapling assembly including: (i) a deck member having a deck surface that faces distally and includes a plurality of staple openings configured to receive a plurality of staples, and (ii) a knife member having a distal end that defines a cutting edge; and (b) an anvil configured to cooperate with the stapling assembly to compress, staple, and cut tissue, wherein the anvil includes: (i) an anvil surface having a plurality of staple forming pockets configured to form the staples, and (ii) a washer positioned adjacent to the anvil surface and having a proximal face, wherein the cutting edge of the knife member is configured to cut through the tissue and the proximal face when the surgical instrument is fired, wherein the proximal face includes a tissue gripping feature configured to stabilize and inhibit the tissue from translating across the washer and the anvil surface during firing.

Example 2

The surgical instrument of Example 1, wherein the tissue griping feature comprises at least one projection extending proximally from the proximal face of the washer.

Example 3

The surgical instrument of any of the preceding Examples, wherein the tissue gripping feature includes at least one of a rough surface, an annular ridge, or a plurality of nubs.

Example 4

The surgical instrument of any of the preceding Examples, wherein the washer includes a proximal wall that presents the proximal face, wherein a central portion of the proximal wall includes at least one of an arched portion, a peaked portion, a tapered portion, or a grooved portion.

Example 5

The surgical instrument of Example 4, wherein the central portion of the proximal wall has a smaller thickness than adjacent outer portions of the proximal wall

Example 6

The surgical instrument of any of the preceding Examples, wherein the washer includes an annular projection distal of the proximal face.

Example 7

The surgical instrument of any of the preceding Examples, wherein the washer includes a proximal wall that presents the proximal face, wherein the proximal wall has a coating on a proximal side or a distal side of the proximal wall.

Example 8

The surgical instrument of any of the preceding Examples, wherein the tissue gripping feature includes a first tissue gripping feature positioned along first portion of the proximal face and a second tissue gripping feature positioned along a second portion of the proximal face, wherein the first and second tissue gripping features are spaced apart from one another in a direction transverse to a longitudinal axis of the surgical instrument.

Example 9

The surgical instrument of any of the preceding Examples, wherein the washer includes a plurality of washer protrusions positioned along the proximal face and the deck member includes a plurality of deck protrusions positioned along the deck surface, wherein the plurality of washer protrusions and deck protrusions are configured to cooperate to grip and stabilize tissue during firing of the surgical instrument.

Example 10

The surgical instrument of any of the preceding Examples, wherein the washer is annular and includes a proximal wall that presents the proximal face, wherein the washer further includes a radially inner wall and a radially outer wall that are spaced apart from one another and are interconnected by the proximal wall, wherein at least a portion of the proximal wall has a thickness that is smaller than a thickness of each of the radially inner wall and the radially outer wall to promote cutting of the proximal wall by the knife member.

Example 11

The surgical instrument of any of the preceding Examples, wherein the stapling assembly further includes an auxiliary tissue compression member positioned adjacent to the knife member, wherein the auxiliary tissue compression member is configured to compress tissue distally against the proximal face of the washer when the surgical instrument is fired to thereby stabilize and inhibit the tissue from translating across the washer and the anvil surface during firing.

Example 12

The surgical instrument of Example 11, wherein each of the knife member and the auxiliary tissue compression member is cylindrical, wherein the auxiliary tissue compression member has a maximum outer diameter that is less than an outer diameter of the knife member.

Example 13

The surgical instrument of any of Examples 11 through 12, wherein at least a distal end of the auxiliary tissue compression member is translatable proximally relative to the knife member as the knife member advances distally to cut tissue.

Example 14

The surgical instrument of any of Examples 11 through 13, wherein the auxiliary tissue compression member comprises at least one of a translatable member or a resiliently compressible member.

Example 15

The surgical instrument of any of the preceding Examples, wherein the deck member is annular and the staple openings are arranged in a plurality of annular arrays on the deck surface, wherein the anvil surface is annular and the stable forming pockets are arranged in a plurality of annular arrays on the anvil surface, wherein the washer is annular and is positioned radially inwardly of the anvil surface.

Example 16

A surgical instrument comprising: (a) a stapling assembly including: (i) a housing extending distally along a central axis, (ii) a deck member including a deck surface having an annular array of staple openings configured to receive a plurality of staples, and (iii) a knife member disposed within the housing, wherein a distal end of the knife member includes a cutting edge; and (b) an anvil configured to selectively couple with the stapling assembly to compress, staple, and cut tissue, wherein the anvil includes: (i) an anvil surface including a plurality of staple forming pockets configured to form the staples, (ii) an annular recess positioned radially inwardly of the anvil surface, and (iii) a breakable member positioned within the annular recess and having a proximal face, wherein the cutting edge of the knife member is configured to cut through the tissue and the proximal face when the surgical instrument is fired, wherein the proximal face includes a tissue gripping feature that extends toward the deck surface and is configured to stabilize the tissue in a radial direction of the anvil during firing.

Example 17

A surgical instrument comprising: (a) a stapling assembly comprising: (i) a deck surface including a plurality of staple openings configured to receive a plurality of staples, (ii) a knife member having a distal end that defines a cutting edge, and (iii) an auxiliary tissue compression member positioned adjacent to the knife member and separately from the deck surface; and (b) an anvil operatively coupled with the stapling assembly, wherein the anvil comprises: (i) an anvil surface including a plurality of staple forming pockets, wherein the anvil surface is configured to align and cooperate with the deck surface to compress and staple tissue, and (ii) a washer positioned adjacent to the anvil surface, wherein the cutting edge of the knife member is configured to cut through the tissue and a proximal face of the washer when the surgical instrument is fired, wherein a distal end of the auxiliary tissue compression member is configured to compress tissue distally against at least one of the anvil surface or the proximal face of the washer and thereby stabilize and inhibit the tissue from translating across the washer and the anvil surface during firing.

Example 18

The surgical instrument of Example 17, wherein at least the distal end of the auxiliary tissue compression member is movable proximally relative to the knife member when the cutting edge is driven distally through the tissue and the proximal face of the washer.

Example 19

The surgical instrument of any of Examples 17 through 18, wherein the auxiliary tissue compression member includes at least one of: (A) a resiliently compressible member having resilient splines configured to be compressed proximally when the surgical instrument is closed on tissue to deliver a distal compression force to tissue at a location adjacent to the knife member, or (B) a translatable member configured to translate distally with the knife member during firing to deliver a distal compression force to tissue at a location adjacent to the knife member.

Example 20

The surgical instrument of any of Examples 17 through 19, wherein each of the knife member and the auxiliary tissue compression member is cylindrical, wherein the auxiliary tissue compression member is positioned radially inwardly of the knife member.

VII. MISCELLANEOUS

While exemplary features are disclosed herein in connection with circular surgical staplers, it will be appreciated that one or more of the exemplary features, including the tissue gripping features and the auxiliary tissue compression members, may be employed with other types of surgical staplers as well, such as surgical staplers of the type disclosed in U.S. Pat. No. 10,045,780, entitled "Method of Applying Staples in Lower Anterior Bowel Resection," issued Aug. 14, 2018; and U.S. Pub. No. 2020/0337700, entitled "Cartridge Based Lockout Mechanism for Right Angle Surgical Stapler," published Oct. 29, 2020, issued as U.S. Pat. No. 11,324,504 on May 10, 2022, the disclosures of which are incorporated by reference herein.

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
    (a) a stapling assembly including:
        (i) a deck member having a deck surface that faces distally and includes a plurality of staple openings configured to receive a plurality of staples, and
        (ii) a knife member having a distal end that defines a cutting edge; and
    (b) an anvil configured to cooperate with the stapling assembly to compress, staple, and cut tissue, wherein the anvil includes:
        (i) an anvil surface having a plurality of staple forming pockets configured to form the staples, and
        (ii) a washer positioned adjacent to the anvil surface and having a proximal face, wherein the cutting edge of the knife member is configured to cut through the tissue and the proximal face when the surgical instrument is fired,
        wherein the proximal face includes a tissue gripping feature configured to stabilize and inhibit the tissue from translating across the washer and the anvil surface during firing.

2. The surgical instrument of claim 1, wherein the tissue griping feature comprises at least one projection extending proximally from the proximal face of the washer.

3. The surgical instrument of claim 1, wherein the tissue gripping feature includes at least one of a rough surface, an annular ridge, or a plurality of nubs.

4. The surgical instrument of claim 1, wherein the washer includes a proximal wall that presents the proximal face, wherein a central portion of the proximal wall includes at least one of an arched portion, a peaked portion, a tapered portion, or a grooved portion.

5. The surgical instrument of claim 4, wherein the central portion of the proximal wall has a smaller thickness than adjacent outer portions of the proximal wall.

6. The surgical instrument of claim 1, wherein the washer includes an annular projection distal of the proximal face.

7. The surgical instrument of claim 1, wherein the washer includes a proximal wall that presents the proximal face, wherein the proximal wall has a coating on a proximal side or a distal side of the proximal wall.

8. The surgical instrument of claim 1, wherein the tissue gripping feature includes a first tissue gripping feature positioned along a first portion of the proximal face and a second tissue gripping feature positioned along a second portion of the proximal face, wherein the first and second tissue gripping features are spaced apart from one another in a direction transverse to a longitudinal axis of the surgical instrument.

9. The surgical instrument of claim 1, wherein the washer includes a plurality of washer protrusions positioned along the proximal face and the deck member includes a plurality of deck protrusions positioned along the deck surface, wherein the plurality of washer protrusions and deck protrusions are configured to cooperate to grip and stabilize tissue during firing of the surgical instrument.

10. The surgical instrument of claim 1, wherein the washer is annular and includes a proximal wall that presents the proximal face, wherein the washer further includes a radially inner wall and a radially outer wall that are spaced apart from one another and are interconnected by the proximal wall, wherein at least a portion of the proximal wall has a thickness that is smaller than a thickness of each of the radially inner wall and the radially outer wall to promote cutting of the proximal wall by the knife member.

11. The surgical instrument of claim 1, wherein the stapling assembly further includes an auxiliary tissue compression member positioned adjacent to the knife member, wherein the auxiliary tissue compression member is configured to compress tissue distally against the proximal face of the washer when the surgical instrument is fired to thereby stabilize and inhibit the tissue from translating across the washer and the anvil surface during firing.

12. The surgical instrument of claim 11, wherein each of the knife member and the auxiliary tissue compression member is cylindrical, wherein the auxiliary tissue compression member has a maximum outer diameter that is less than an inner diameter of the knife member.

13. The surgical instrument of claim 11, wherein at least a distal end of the auxiliary tissue compression member is translatable proximally relative to the knife member as the knife member advances distally to cut tissue.

14. The surgical instrument of claim 11, wherein the auxiliary tissue compression member comprises at least one of a translatable member or a resiliently compressible member.

15. The surgical instrument of claim 1, wherein the deck member is annular and the staple openings are arranged in a plurality of annular arrays on the deck surface, wherein the anvil surface is annular and the stable forming pockets are arranged in a plurality of annular arrays on the anvil surface, wherein the washer is annular and is positioned radially inwardly of the anvil surface.

16. A surgical instrument comprising:
(a) a stapling assembly including:
    (i) a housing extending distally along a central axis,
    (ii) a deck member including a deck surface having an annular array of staple openings configured to receive a plurality of staples, and
    (iii) a knife member disposed within the housing, wherein a distal end of the knife member includes a cutting edge; and
(b) an anvil configured to selectively couple with the stapling assembly to compress, staple, and cut tissue, wherein the anvil includes:
    (i) an anvil surface including a plurality of staple forming pockets configured to form the staples,
    (ii) an annular recess positioned radially inwardly of the anvil surface, and
    (iii) a breakable member positioned within the annular recess and having a proximal face, wherein the cutting edge of the knife member is configured to cut through the tissue and the proximal face when the surgical instrument is fired,
    wherein the proximal face includes a tissue gripping feature that extends toward the deck surface and is configured to stabilize the tissue in a radial direction of the anvil during firing.

17. A surgical instrument comprising:
(a) a stapling assembly comprising:
    (i) a deck surface including a plurality of staple openings configured to receive a plurality of staples,
    (ii) a knife member having a distal end that defines a cutting edge, and
    (iii) an auxiliary tissue compression member positioned adjacent to the knife member and separately from the deck surface; and
(b) an anvil operatively coupled with the stapling assembly, wherein the anvil comprises:
    (i) an anvil surface including a plurality of staple forming pockets, wherein the anvil surface is configured to align and cooperate with the deck surface to compress and staple tissue, and
    (ii) a washer positioned adjacent to the anvil surface, wherein the cutting edge of the knife member is configured to cut through the tissue and a proximal face of the washer when the surgical instrument is fired,
    wherein a distal end of the auxiliary tissue compression member is configured to compress tissue distally against at least one of the anvil surface or the proximal face of the washer and thereby stabilize and inhibit the tissue from translating across the washer and the anvil surface during firing.

18. The surgical instrument of claim 17, wherein at least the distal end of the auxiliary tissue compression member is movable proximally relative to the knife member when the cutting edge is driven distally through the tissue and the proximal face of the washer.

19. The surgical instrument of claim 17, wherein the auxiliary tissue compression member includes at least one of:
(A) a resiliently compressible member having resilient splines configured to be compressed proximally when the surgical instrument is closed on tissue to deliver a distal compression force to tissue at a location adjacent to the knife member, or (B) a translatable member configured to translate distally with the knife member during firing to deliver a distal compression force to tissue at a location adjacent to the knife member.

20. The surgical instrument of claim 17, wherein each of the knife member and the auxiliary tissue compression member is cylindrical, wherein the auxiliary tissue compression member is positioned radially inwardly of the knife member.

\* \* \* \* \*